US010093985B2

(12) United States Patent
Sanders et al.

(10) Patent No.: US 10,093,985 B2
(45) Date of Patent: Oct. 9, 2018

(54) METHODS FOR DETECTING GENE DYSREGULATION BY INTRAGENIC DIFFERENTIAL EXPRESSION

(71) Applicant: Quest Diagnostics Investments Incorporated, Wilmington, DE (US)

(72) Inventors: Heather R. Sanders, Winchester, CA (US); Maher Albitar, Coto De Caza, CA (US); Aurelia Meloni-Ehrig, Gainesville, VA (US)

(73) Assignee: Quest Diagnostics Investments Incorporated, Wilmington, DE (US)

( * ) Notice: Subject to any disclaimer, the term of this patent is extended or adjusted under 35 U.S.C. 154(b) by 0 days.

(21) Appl. No.: 15/372,752

(22) Filed: Dec. 8, 2016

(65) Prior Publication Data
US 2017/0152572 A1 Jun. 1, 2017

Related U.S. Application Data

(63) Continuation of application No. 14/699,380, filed on Apr. 29, 2015, now Pat. No. 9,546,404, which is a continuation of application No. 14/454,124, filed on Aug. 7, 2014, now Pat. No. 9,187,788, which is a continuation of application No. 13/848,974, filed on Mar. 22, 2013, now Pat. No. 8,815,516, which is a continuation of application No. 12/786,266, filed on May 24, 2010, now Pat. No. 8,426,133.

(60) Provisional application No. 61/181,217, filed on May 26, 2009.

(51) Int. Cl.
*C12P 19/34* (2006.01)
*C12Q 1/6886* (2018.01)
*C12Q 1/6809* (2018.01)
*C12Q 1/6858* (2018.01)

(52) U.S. Cl.
CPC ......... *C12Q 1/6886* (2013.01); *C12Q 1/6809* (2013.01); *C12Q 1/6858* (2013.01); *C12Q 2600/156* (2013.01); *C12Q 2600/158* (2013.01); *C12Q 2600/16* (2013.01)

(58) Field of Classification Search
USPC .............................. 435/6.12, 91.2
See application file for complete search history.

(56) References Cited

U.S. PATENT DOCUMENTS

| | | | |
|---|---|---|---|
| 5,529,925 A | 6/1996 | Morris et al. | |
| 5,695,995 A | 12/1997 | Weintraub et al. | |
| 5,770,421 A * | 6/1998 | Morris | C07K 14/47 435/194 |
| 5,968,734 A * | 10/1999 | Aurias | C07K 14/47 435/6.14 |
| 6,444,419 B1 | 9/2002 | Wong et al. | |
| 6,451,997 B1 | 9/2002 | Morris et al. | |
| 6,902,892 B1 | 6/2005 | Salceda et al. | |
| 7,037,667 B1 | 5/2006 | Afar et al. | |
| 7,189,833 B2 * | 3/2007 | Cohen | C07K 14/47 435/6.14 |
| 7,432,064 B2 | 10/2008 | Salceda et al. | |
| 7,718,369 B2 | 5/2010 | Tomlins et al. | |
| 8,426,133 B2 | 4/2013 | Sanders et al. | |
| 8,815,516 B2 | 8/2014 | Sanders et al. | |
| 2003/0096255 A1 | 5/2003 | Felix et al. | |
| 2003/0185830 A1 | 10/2003 | Xu et al. | |
| 2004/0259086 A1 | 12/2004 | Schlegel et al. | |
| 2005/0191673 A1 | 9/2005 | Schlegel et al. | |
| 2005/0227917 A1 | 10/2005 | Williams et al. | |
| 2006/0068425 A1 | 3/2006 | Monahan et al. | |
| 2006/0115821 A1 | 6/2006 | Einstein et al. | |
| 2007/0048738 A1 | 3/2007 | Donkena et al. | |
| 2007/0212702 A1 | 9/2007 | Tomlins et al. | |
| 2007/0237770 A1 | 10/2007 | Lai et al. | |
| 2008/0070797 A1 | 3/2008 | Mounts | |
| 2008/0131876 A1 | 6/2008 | Hantash | |
| 2008/0260761 A1 | 10/2008 | Vartanian et al. | |
| 2008/0269157 A1 | 10/2008 | Srivastava et al. | |
| 2009/0136942 A1 | 5/2009 | Kopreski | |
| 2009/0142262 A1 | 6/2009 | Salceda et al. | |
| 2009/0170075 A1 | 7/2009 | Petrovics et al. | |
| 2009/0181378 A1 | 7/2009 | Sanders et al. | |
| 2009/0208937 A1 | 8/2009 | Chinnaiyan et al. | |
| 2009/0226921 A1 | 9/2009 | Afar et al. | |

(Continued)

FOREIGN PATENT DOCUMENTS

WO  WO 2005/111235 A2  11/2005
WO  WO-2008/063769     5/2008

(Continued)

OTHER PUBLICATIONS

Rychlik et al., Nucleic Acids Research 17(21), 8543-8551 (1989).*
Hafner et al, Isothermal Amplification and Multimerization of DNA by Bst DNA Polymerase, Biotechniques, 30(4):852-860 (2001).
Han et al, Characterization of ETS gene aberrations in select histologic variants of prostate carcinoma, Mod Pathol, 22: 1176-1185 (2009).
International Search Report dated Mar. 9, 2011 in application PCT/US2010/061773.
International Search Report dated Sep. 20, 2010 in application PCT/US2009/035974.
Laxman et al, Nonivasive detection of TMPRSS2:ERG fusion transcripts in the urine of men with prostate cancer, (2006), Neoplasia, 8(10):885-888.
Lin et al. Prostate-localized and Androgen-regulated Expression of the Membrane-bound Serine Protease TMPRSS2, Cancer Research 59, 4180-4184 (1999).
Mani, et al, Induced chromosomal proximity and gene fusions in prostate cancer, Science, (2009), 326(5957):1230.

(Continued)

*Primary Examiner* — Kenneth R Horlick
(74) *Attorney, Agent, or Firm* — Foley & Lardner LLP

(57) ABSTRACT

Described herein are methods, compositions and kits directed to the detection of gene dysregulations such as those arising from gene fusions and/or chromosomal abnormalities, e.g., translocations, insertions, inversions and deletions. Samples containing dysregulated gene(s) of interest may show independent expression patterns for the 5' and 3' regions of the gene. The methods, compositions and kits are useful for detecting mutations that cause the differential expression of a 5' portion of a target gene relative to the 3' region of the target gene.

9 Claims, 5 Drawing Sheets

Specification includes a Sequence Listing.

(56) References Cited

U.S. PATENT DOCUMENTS

2009/0239221 A1    9/2009   Chinnaiyan et al.
2012/0202214 A1    8/2012   Omi

FOREIGN PATENT DOCUMENTS

WO    WO 2009/000912 A2    12/2008
WO    WO-2009/102446    8/2009

OTHER PUBLICATIONS

Mao et al, Detection of TMPRSS2:ERG fusion gene in circulating prostate cancer cells, (2008), Asian J Andrology, 10(3):467-473.
Nam et al, Expression of the TMPRSS2:ERG fusion gene predicts cancer recurrence after surgery for localised prostate cancer, British Journal of Cancer, (2007), 97:1690-1695.
Perner et al, EML4-ALK fusion lung cancer: a rare acquired event, Neoplasia, 10(3):298-302, 2008.
Pflueger et al, N-myc downstream regulated gene 1 (NDRG1) is fused to ERG in prostate cancer, Neoplasia, (2009), 11(8):804-811.
Rubin et al, Bioinformatics approach leads to the discovery of the TMPRSS2:ETS gene fusion in prostate cancer, (2006), Lab Investigation, 86:1099-1102.
Rubin et al, The basic biology of HER2, Annals of Oncology, 12(Suppl 1):S3-S8, 2001.
Shappell, Clinical utility of prostate carcinoma molecular diagnostic tests, Rev Urology, (2008), 10(1):44-69.
Tefferi et al, Chronic Myeloid Leukemia: Current Application of Cytogenetics and Molecular Testing for Diagnosis and Treatment, Mayo Clin Proc, 80(3):390-402, 2005.
Tomlins et al, Recurrent fusion of TMPRSS2 and ETS transcription factor genes in prostate cancer, Science (2005), 310(5748): 644-648.
Ueda et al, Amplification of the MYC Gene in Osteosarcoma Secondary to Paget's Disease of Bone; Sarcoma, 1(3-4):131-134, 1997.
Underwood et al, C-erbB-2 gene amplification: a molecular marker in recurrent bladder tumors?, Cancer Res., 55:2422-2430, 1995.
Vega et al, Chromosomal Translocations Involved in Non-Hodgkin Lymphomas, Arch Pathol Lab Med, 127:1148-1160, 2003.
Wharam et al, Specific detection of DNA and RNA targets using a novel isothermal nucleic acid amplification assay based on the formation of a three-way junction structure, Nucleic Acids Res, 29(11):E54-E54, (2001).
Wright et al. "Newer Potential Biomarkers in Prostate Cancer", Reviews in Urology 9(4):207-213 (2007).
Zhang et al., Characterization of Genomic Breakpoints in MLL and CBP in Leukemia Patients with t(11;16), Genes, Chromosomes Cancer, 41:257-65, 2004.
Zhang et al., E Protein Silencing by the Leukemogenic AML1-ETO Fusion Protein, Science, 305:1286-1289, 2004.
Office Action issued by the Examiner in U.S. Appl. No. 12/975,908 dated Aug. 16, 2012.
Soverini et al., "Cycline D1 overexpression is a favorable prognostic variable for newly diagnosed multiple myeloma patients treated with high-dose chemotherapy and single or double autologous transplantation," Blood, vol. 102, pp. 1588-1594, 2003.
New England BioLabs Catalogue, pp. 121 and 284, 1999.
Ar-Rushdi et al., "Differential Expression of the Translocated and the Untranslocated c-myc Oncogene in Burkitt Lymphoma," Science, vol. 222, pp. 390-393, 1983.
Office Action dated May 18, 2012 by the Examiner in U.S. Appl. No. 12/786,266.
Notice of Allowance dated Aug. 30, 2012 by the Examiner in U.S. Appl. No. 12/286,266.
Notice of Allowance dated Dec. 28, 2012 by the Examiner in U.S. Appl. No. 12/286,266.
Sanders et al., "Intragenic expression profile in tissue and plasma for the detection of TMPRSS2 rearrangements associated with prostate cancer," Journal of Clinical Onocology, vol. 27, No. 15S, p. 5162, May 20, 2009.
Sanders et al., "Detection of various ALK translocations using intragenic differential expression (IDE) in patients with non-small cell lung cancer," Proceedings o0f the Annual Meeting of the American Association for Cancer Research, vol. 51, p. 910, Apr. 2010.
Choi et al., "Identification of Novel Isoforms of the EML4-ALK Transforming Gene in Non-Small Cell Lung Cancer," Cancer Research, vol. 68, No. 13, pp. 4971-4976, Jul. 1, 2008.
European Search Report issued in application No. EP 10 78 1063.2 dated Mar. 4, 2013.
Notice of Allowance issued in U.S. Appl. No. 12/975,908 dated Jun. 3, 2013.
Office Action dated Dec. 3, 2013 in U.S. Appl. No. 13/848,974.
Notice of Allowance dated Apr. 21, 2014 in U.S. Appl. No. 13/848,974.
Office Action dated Sep. 22, 2014 in U.S. Appl. No. 14/021,363.
Soda et al., "Identification of the transforming EML4-ALK fusion gene in non-small-cell lung cancer," Nature, vol. 448, pp. 561-567, Aug. 2, 2007.
Office Action dated Jan. 27, 2015 in U.S. Appl. No. 14/454,124.
Office Action dated May 9, 2016 in U.S. Appl. No. 14/699,380.
Notice of Allowance dated Sep. 9, 2016 in U.S. Appl. No. 14/699,380.
Mehra et al., "Comprehensive assessment of TMPRSS2 and ETS family gene aberrations in clinically localized prostate cancer," Modern Pathology, vol. 20, pp. 538-544, Mar. 2007.
Helgeson et al., "Characterization of TMPRSS2:ETV5 and SLC45A3:ETV5 Gene Fusions in Prostate Cancer," Cancer Research, vol. 68, No. 1, pp. 73-80, Jan. 2008.
Tomlins et al., "TMPRSS2:ETV4 Gene Fusions Define a Third Molecular Subtype of Prostate Cancer," Cancer Research, vol. 66, No. 7, pp. 3396-3400, Apr. 2006.
European Search Report dated Jan. 17, 2017 in application No. EP 16 17 8796.

\* cited by examiner

SEQUENCE LISTING

```
<160> NUMBER OF SEQ ID NOS: 18

<210> SEQ ID NO 1
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 1
taggcgcgag ctaagcagga                                                 20

<210> SEQ ID NO 2
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 2
cctgccgcgc tccaggcgg                                                  19

<210> SEQ ID NO 3
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
aggcggaggc ggagggcgag gggc                                            24
```

<210> SEQ ID NO 4
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 4
tggtgcgagg gaagcaat                                                  18

<210> SEQ ID NO 5
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cacccaatgt gcaggtgga                                                 19

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
aaaggaactt gccctgagca ctcc                                           24

<210> SEQ ID NO 7
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
catccgctct aaacaacctc a                                              21

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
ggccataatg cgatcaagtt                                                20

<210> SEQ ID NO 9
<211> LENGTH: 22
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
ctttctggtc agagagaagc aa                                             22

<210> SEQ ID NO 10
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
ccaggtgaat ggctcaagga a                                             21

<210> SEQ ID NO 11
<211> LENGTH: 18
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gggctgccca ccatcttc                                                 18

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
tctcctgatg aatgcagtgt ggcc                                          24

<210> SEQ ID NO 13
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 13
cccaactttg ccatcatttt                                               20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
gcaaagcggt gttgattaca                                               20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 15
tgaatactgc acccaggacc                                               20

```
<210> SEQ ID NO 16
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
tggcttttga caatatctcc a                                                  21

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
tgcaggatct tgtcctctcc                                                    20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 18
agcctggact gctacctcac                                                    20
```

METHODS FOR DETECTING GENE DYSREGULATION BY INTRAGENIC DIFFERENTIAL EXPRESSION

CROSS-REFERENCE TO RELATED APPLICATION

This application is a continuation of U.S. patent application Ser. No. 14/699,380, filed Apr. 29, 2015, now U.S. Pat. No. 9,546,404, which is a continuation of U.S. patent application Ser. No. 14/454,124, filed Aug. 7, 2014, now U.S. Pat. No. 9,187,788, which is a continuation of U.S. patent application Ser. No. 13/848,974, filed Mar. 22, 2013, now U.S. Pat. No. 8,815,516, which is a continuation of U.S. patent application Ser. No. 12/786,266, filed May 24, 2010, now U.S. Pat. No. 8,426,133, which claims the benefit of U.S. Provisional Application No. 61/181,217 filed on May 26, 2009, all of which are hereby incorporated by reference in their entirety.

TECHNICAL FIELD

The present technology relates generally to detection of gene dysregulations such as those arising from gene fusions and chromosomal abnormalities, which may be associated with various diseases. In a particular aspect, the present technology relates to the detection of gene deregulations using multiplex quantitative RT-PCR.

BACKGROUND

The following description is provided to assist the understanding of the reader. None of the information provided or references cited is admitted to be prior art to the present invention.

Variations in chromosome structure involve changes in parts of chromosomes rather than changes in the number of chromosomes or sets of chromosomes in the genome. There are four common types of mutations: deletions and duplications (both of which involve a change in the amount of DNA on a chromosome), inversions (which involve a change in the arrangement of a chromosomal segment), and translocations (which involve a change in the location of a chromosomal segment). All four classes of chromosomal structure mutations are initiated by one or more breaks in the chromosome. If a break occurs within a gene, then a gene mutation has been produced, the consequence of which depends on the function of the gene and the time of its expression. Wherever the break occurs, the breakage process leaves broken ends, which may adhere to other broken chromosome ends or the normal ends of other chromosomes.

Reciprocal and Robertsonian translocations are the most frequently occurring types of translocations. Reciprocal translocations usually involve a two-way exchange between different chromosomes. The chromosomes break apart and segments below the break points swap positions. If the event is balanced, no net gain or loss of genetic material results and the individual is usually phenotypically unaffected if no genes are disrupted.

Robertsonian translocations occur when two chromosomes fuse at the centers and essentially combine into one. Most of the genetic material remains from both chromosomes. As in balanced reciprocal translocations, the carrier may be normal, but produce genetically unbalanced gametes. Most progeny originating from unbalanced gametes do not survive and a miscarriage occurs during early pregnancy. If the carrier is fertile and progeny survive, various defects could occur. One Robertsonian translocation results in the fusion of chromosomes 14 and 21. Resulting progeny may inherit three copies of chromosome 21 which causes Down's syndrome.

Genetic abnormalities such as duplication, deletion, chromosomal translocation, and point mutation often lead to pathological conditions. Some diseases, such as cancer, are due to genetic abnormalities acquired in a few cells during life, while in other diseases the genetic abnormality is present in ail cells of the body and present since conception.

SUMMARY OF THE INVENTION

Described herein are methods, compositions, and kits directed to the detection of gene dysregulations such as those arising from gene fusions and chromosomal abnormalities, translocations, insertions, inversions and deletions. The methods, compositions and kits are useful for detecting mutations that cause the differential expression of a 5' region of a target gene relative to the 3' region of the target gene.

In one aspect, the present disclosure provides a method for detecting a dysregulation in a target gene. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs. The method may also provide that a difference in the amounts of amplification products produced by steps (a) and (b) indicates that the target gene is dysregulated.

In another aspect, the present disclosure provides a method for detecting the presence or absence of a dysregulation in a target gene in a sample. The method may include: (a) measuring the amount of transcription of a 5' region of the target gene and a 3' region of the target gene in the test sample; and (b) comparing the relative expression of the 5' region to the 3' region of the target gene in the test sample to the relative expression of the 5' region to the 3' region of the target gene in a reference sample. The method may also provide that a difference in the relative expression in the test sample compared to the reference sample is indicative of the presence of a gene dysregulation. In an embodiment, the relative amount of transcript can be determined using real-time PCR and comparing the threshold cycle, or Ct, value, for each amplicon. The Ct value can be normalized to a reference sample.

In another aspect, the disclosure provides a method for diagnosing cancer or a susceptibility to cancer in a subject. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs. The method may also provide that a difference in the amounts of amplification products produced by steps (a) and (b) indicates that the subject has cancer or is susceptible to cancer resulting from a gene dysregulation.

In another aspect, the disclosure provides a method for diagnosing prostate cancer or a susceptibility to prostate cancer in a subject. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs. The method may also provide that a difference in the amounts of amplification products produced by steps (a) and (b) indicates that the target gene is dysregulated.

In another aspect, the disclosure provides a method for diagnosing non-small cell lung carcinoma (NSCLC) or a susceptibility to NSCLC in a subject. The method may include: (a) amplifying a 5' region of the target gene transcript, if present, in a biological sample with one or more 5' target primer pairs which are complementary to the 5' region of the target gene; (b) amplifying a 3' region of the target gene transcript, if present, in the biological sample with one or more 3' target primer pairs which are complementary to the 3' region of the target gene; and (c) detecting the amounts of amplification product produced by the one or more 5' target primer pairs and the one or more 3' target primer pairs, the method may also provide that a difference in the amounts of amplification products produced by steps (a) and (b) indicates that the target gene is dysregulated. Suitable target genes include, for example, ALK, and EML4.

Optionally, the nucleic acid sample containing the target gene of interest may be subjected to another analysis to determine the nature of the gene dysregulation. Suitable analyses include, for example, comparative hybridization (e.g., comparative genomic hybridization). Comparative hybridization techniques such as comparative genomic hybridization (CGH) is limited by the fact that this technique is only able to detect unbalanced rearrangements (rearrangements that lead to gain or loss of genetic material). Comparative hybridization cannot adequately detect chromosomal abnormalities such as balanced translocations. Thus, any of the methods of the invention may be used in combination with a comparative hybridization technique. In particular, the primary abnormality in most leukemias, lymphomas, and solid tumors is a balanced translocation. The combination of the inventive methods with comparative hybridization (e.g., CGH) will be able to detect both balanced and unbalanced rearrangements and provide a more accurate diagnosis than if the comparative hybridization technique was used alone. In the case of unbalanced rearrangements, the comparative hybridization technique may be used as a confirmatory assay. As discussed herein, target gene dysregulations may arise from gene fusions and chromosomal abnormalities including, for example, translocations, deletions, inversions, and insertions.

Suitable target genes for use with any of the foregoing methods include, for example, Transmembrane Protease Serine 2 (TMPRSS2), ETS Related Gene (ERG), ETS translocation variant 1 (ETV1), Solute Carrier Family 45, Member 3 (SLC45A3), Human Endogenous Retrovirus K (HERV-K_22q11.3), Chromosome 15 Open Reading Frame 21 (C15ORF21), Heterogeneous Nuclear Ribonucleoproteins A2/B1 (HNRPA2B1), ETS Translocation Variant 4 (ETV4), ETS Translocation Variant 5 (ETV5), Anaplastic lyimphoma kinase (ALK), or Echinoderm microtubule associated protein like 4 (EML4), EUS, RANBP2, PAX, BUS, COLIA1 CLTC, KIF5B FKHR, PDGFB, FEV, DDIT3, ATF1, CREA, SP3, NR4A3, WT1, SYT, SSX1, SSX2, SSX4, BCR, ABL, BCL2, RARA, NPM, and ATIC.

Any cancer or other disorder associated with a gene dysregulation may be diagnosed using any of the foregoing methods. Disorders suitable for diagnosis include, for example, pediatric soft tissue sarcomas that have indeterminate histologies.

In one embodiment, the biological sample is contacted with the one or more 5' target primer pairs and the one or more 3' target primer in a multiplex amplification reaction. In one embodiment, the detecting is accomplished using a labeled oligonucleotide probe complementary to each amplification product. For example, each oligonucleotide probe may include a different detectable label, such as a donor fluorophore and quencher moiety. In another embodiment, at least one of the primers for the 5' region and/or at least one of the primers for the 3' region is detectably labeled, preferably with different detectable labels. In illustrative embodiments, the amplifying is performed using quantitative RT-PCR, e.g., real-time RT-PCR.

In some embodiments, the chromosomal abnormality is selected from the group consisting of: a translocation, a deletion, an inversion, and an insertion. In one embodiment, the biological sample is a sample from a subject to be tested for a chromosomal abnormality.

In one embodiment, the methods further include amplifying a region of an endogenous control gene transcript present in the biological sample with a primer pair complementary to the endogenous control gene and detecting the amplification of the region of the endogenous control gene. In some embodiments, the amount of amplified target gene transcripts (i.e., the 5' region and the 3' region) may be normalized to the amount of amplified endogenous control gene transcript. Suitable endogenous control genes include, for example, ABL.

In embodiments of any of the aspects herein, the method further includes: (a) measuring the amount of transcription of a 5' region of a second target gene and a 3' region of the second target gene in the test sample: and (b) comparing the relative expression of the 5' region to the 3' region of the second target gene in the test sample to the relative expression of the 5' region to the 3' region of the second target gene in a reference sample. The method may also provide that a difference in the relative expression of both the target gene and the second target gene in the test sample compared to the reference sample is indicative of the presence of a target gene: second target gene translocation. Exemplary target gene and second target gene translocations include TMPRSS2:ERG, TMPRSS2:ETV1, and EML4:ALK.

Suitable biological samples include, for example, whole blood, isolated blood cells, plasma, serum, and urine.

In another aspect, the disclosure provides a kit for detecting a genetic abnormality in a sample. The kit may include: (a) at least one oligonucleotide for determining the level of expression of at least one sequence from the 5' region of a target gene; and (b) at least one oligonucleotide for determining the level of expression of at least one sequence from the 3' region of the target gene. In one embodiment, the target gene is TMPRSS2 or ALK. In some embodiments, the kits further include one or more reagents for performing real-time RT-PCR.

Primers, designated by arrows, and probes, designated by lines with circles representing fluorophore and quencher, designed to the 5' and 3' regions of TMPRSS2 are shown. Panel A: schematic representation of TMPRSS2 and Erythroblast Transformation-Specific (ETS) transcripts found in a normal prostate along with the relative transcript level (High/Low). Panel B: schematic representation of TMPRSS2:ETS fusion transcripts found in prostate tumors along with the relative transcript level (High/Low).

Figure 2:
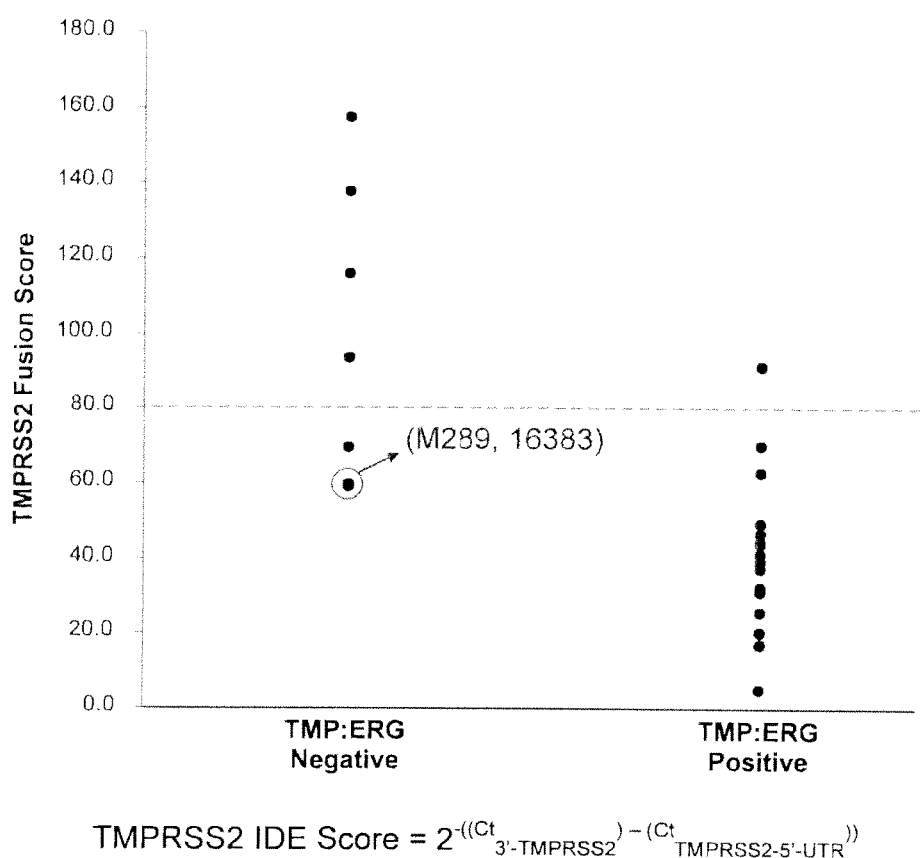

FIG. 2 is a plot showing TMPRSS2 IDE scores of FFPE tumor tissue from 25 prostate cancer patients determined by the equation shown above with Ct values obtained from real-time RT-PCR. Results are grouped by the known TMPRSS2:ERG fusion status confirmed by fluorescent RT-PCR (7 TMP:ERG negative, 18 TMP:ERG positive). Two specimens from the TMPRSS2:ERG Negative group fall below 60 (encircled), one of which (M289) is suspected to have a TMPRSS2:ETV fusion based on ETV expression data (data not shown).

Figure 3A:
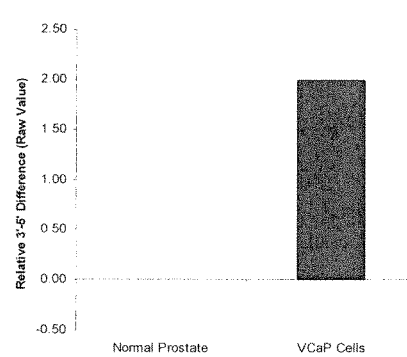
Figure 3B:
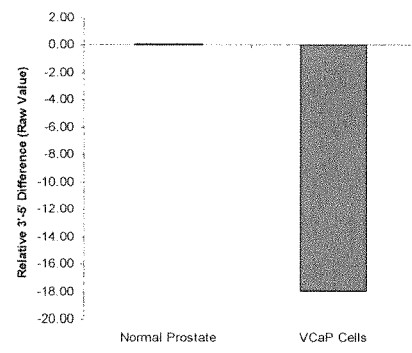

FIG. 3 are bar graphs showing the raw Intragenic Differential Expression (IDE) values for TMPRSS2 (FIG. 3A) and ERG (FIG. 3B) in control specimens (TMPRSS2:ERG prostate cancer cell line). Orientation of 5' and 3' regions are shown by the raw IDE score (absolute value not applied) for TMPRSS2 (FIG. 3A) and ERG (FIG. 3B). Positive values indicate higher 5' levels while negative values indicate higher 3' levels. Normal prostate RNA does not contain TMPRSS2 or ERG fusions, VCaP cell RNA is positive for the TMPRSS2:ERG fusion.

Figure 4:
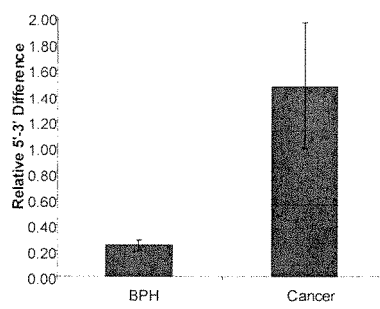

FIG. 4 is a bar graph showing the TMPRSS2 IDE scores in FFPE tissue. Columns indicate average IDE scores from 14 BPH specimens and 30 PCa specimens. Y-error bars represent standard error.

Figure 5:
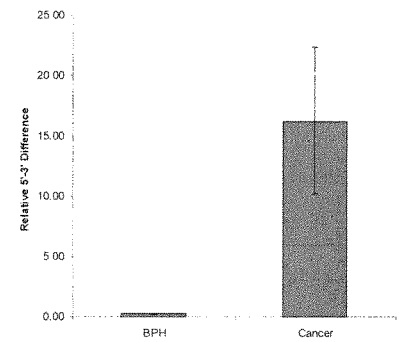

FIG. 5 is a bar graph showing the ERG IDE scores in FFPE tissue. Columns indicate average IDE scores from 14 BPH specimens and 30 PCa specimens. Y-error bars represent standard error.

Figure 6:
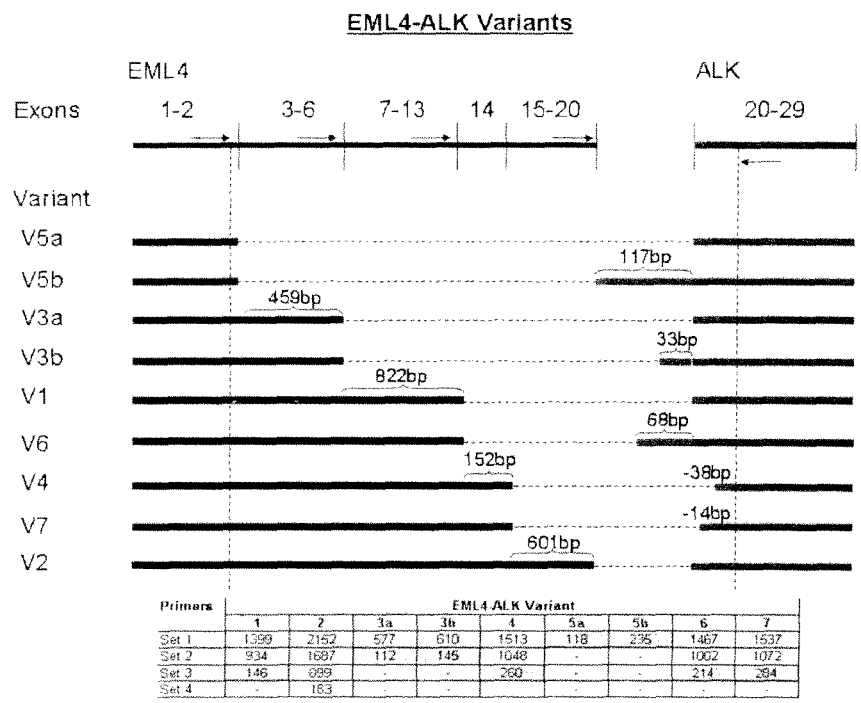

FIG. 6 shows the EML4-ALK fusions detected by direct by RT-PCR and fragment analysis. Right facing arrows indicate forward primers, left facing arrow indicates a reverse FAM-labeled primer. Expected sizes for each variant are indicated in the table.

Figure 7:
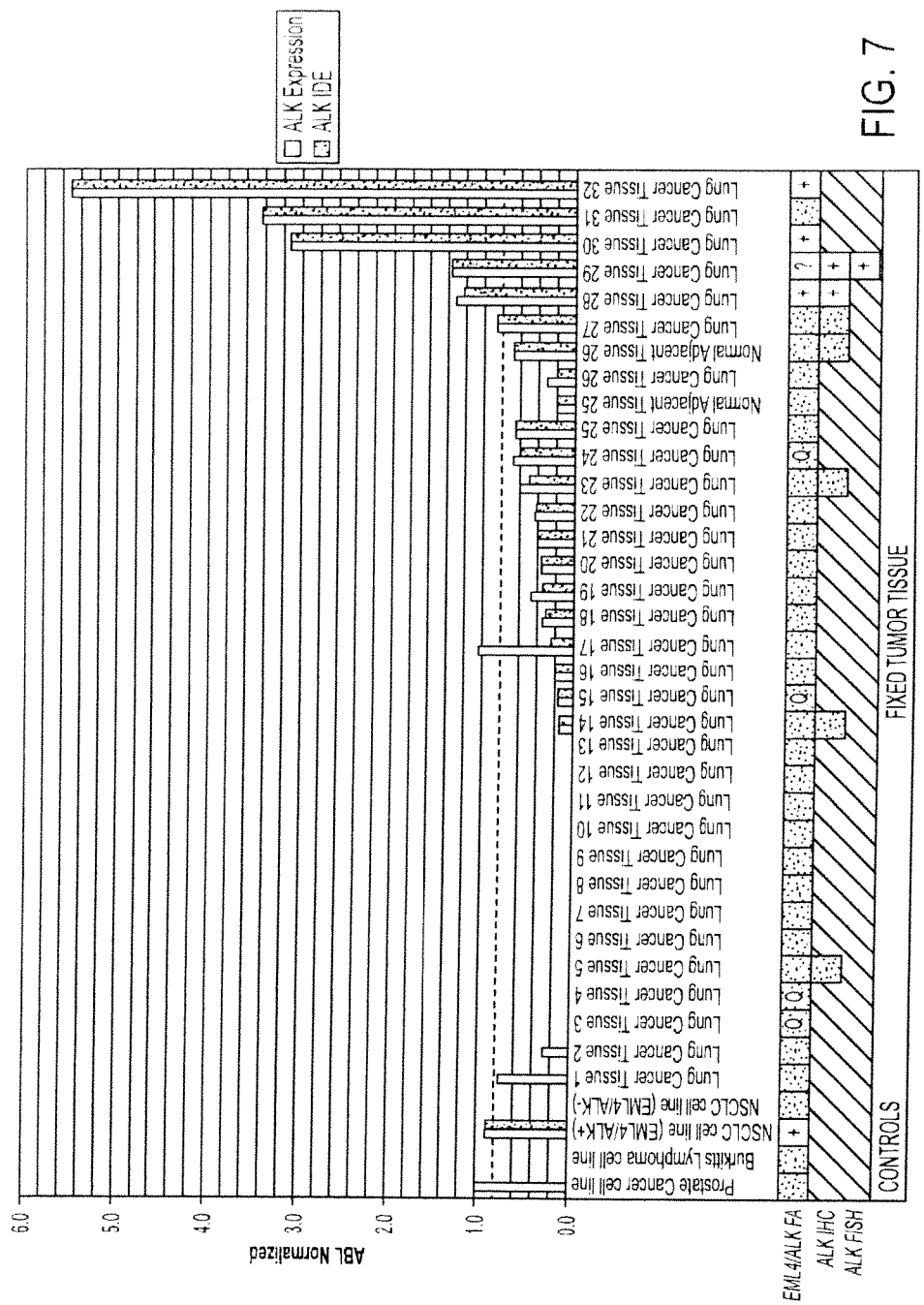

FIG. 7 is a chart comparing detection method results for ALK expression and ALK rearrangement. The bar graph represents ALK expression (light columns) and ALK IDE (dark columns) from four control cell lines and 32 lung cancer tissue specimens. The dotted horizontal line indicates the IDE cutoff level. Results from the EML4:ALK fragment analysis, ALK IHC, and ALK FISH are shown in the table below the graph. Cells with indicate negative result. Cells with "+" indicate positive result. Cells with "Q" indicate insufficient quantity.

DETAILED DESCRIPTION

Described herein are methods, reagents and kits for detecting gene dysregulations such as those arising as a result of chromosomal or genetic abnormalities in a sample, where the dysregulation leads to differential expression or quantities of particular portions of target genes. Chromosomal abnormalities include, for example, translocations, deletions and assertions. Large-scale mutations can affect chromosomal and genetic structure and include, for example, deletions of large chromosomal regions, leading to loss of the genes within those regions; and translocations, which are mutations whose effect is to juxtapose previously separate pieces of DNA, potentially bringing together separate genes to form functionally distinct fusion genes (e.g., TMPRSS2-ERG, TMPRSS2-ETV and EML4-ALK). For example, deletions may result in apposing previously distant genes producing a fusion protein. Another example includes chromosomal inversions, which reverse the orientation of a chromosomal segment. All of these chromosomal abnormalities can disrupt or alter coding sequences or elements in the non-coding region that affect the level of transcription of a particular coding sequence.

To facilitate an understanding of the present invention, a number of terms and phrases are defined below.

As used herein, unless otherwise stated, the singular forms "a," "an," and "the" include plural reference. Thus, for example, a reference to "an oligonucleotide" includes a plurality of oligonucleotide molecules, a reference to label is a reference to one or more labels, a reference to probe is a reference to one or more probes, and a reference to "a nucleic acid" is a reference to one or more polynucleotides.

As used herein, unless indicated otherwise, when referring to a numerical value, the term "about" means plus or minus 10% of the enumerated value.

The terms "amplification" or "amplify" as used herein includes methods for copying a target nucleic acid, thereby increasing the number of copies of a selected nucleic acid sequence. Amplification may be exponential or linear. A target nucleic acid may be either DNA or RNA. The sequences amplified in this manner form an "amplification product." While the exemplary methods described hereinafter relate to amplification using the polymerase chain reaction (PCR), numerous other methods are known in the art for amplification of nucleic acids (e.g., isothermal methods, rolling circle methods, etc.). The skilled artisan will understand that these other methods may be used either in place of, or together with, PCR methods. See, e.g., Saiki, "Amplification of Genomic DNA" in *PCR Protocols*, Innis et al., Eds., Academic Press, San Diego, Calif. 1990, pp. 13-20; Wharam et al., *Nucleic Acids Res.*, 29(11):E54-E54, 2001; Hafner et al., *Biotechniques*, 30(4):852-56, 858, 860, 2001; Zhong et al., *Biotechniques*, 30(4):852-6, 858, 860, 2001.

As used herein, the term "detecting" refers to observing a signal from a detectable label to indicate the presence of a target nucleic acid in the sample. The term detecting dots not require the method to provide 100% sensitivity and/or 100% specificity. As is well known, "sensitivity" is the probability that a test is positive, given that the subject has a target nucleic acid sequence, while "specificity" is the probability that a test is negative, given that the subject does not have the target nucleic acid sequence. A sensitivity of at least 50% is preferred, although sensitivities of at least 60%, at least 70%, at least 80%, at least 90% and at least 99% are clearly more preferred. A specificity of at least 50% is preferred, although sensitivities of at least 60%, at least 70%, at least 80%, at least 90% and at least 99% are clearly more preferred. Detecting also encompasses assays with false positives and false negatives. False negative rates may be 1%, 5%, 10%, 15%, 20% or even higher. False positive rates may be 1%, 5%, 10%, 15%, 20% or even higher.

The terms "complement", "complementary" or "complementarity" as used herein with reference to polynucleotides (i.e., a sequence of nucleotides such as an oligonucleotide or a genomic nucleic acid) related by the base-pairing rules. The complement of a nucleic acid sequence as used herein refers to an oligonucleotide which, when aligned with the nucleic acid sequence such that the 5' end of one sequence is paired with the 3' end of the other, is in "antiparallel association". For example, for the sequence 5'-A-G-T-3' is complementary to the sequence 3'-T-C-A-5'. Certain bases not commonly found in natural nucleic acids may be included in the nucleic acids of the present invention and include, for example, inosine and 7-deazaguanine. Complementarity need not be perfect; stable duplexes may contain mismatched base pairs or unmatched bases. Those skilled in the art of nucleic acid technology can determine duplex stability empirically considering a number of variables including, for example, the length of the oligonucleotide, base composition and sequence of the oligonucleotide, ionic strength and incidence of mismatched base pairs. Complementarity may be "partial" in which only some of the nucleic acids' bases are matched according to the base pairing rules. Or, there may be "complete," "total," or "full" complementarity between the nucleic acids.

The term "detectable label" as used herein refers to a molecule or a compound or a group of molecules or a group of compounds associated with a probe and is used to identify the probe hybridized to a genomic nucleic acid or reference nucleic acid. In some cases, the detectable label may be detected directly. In other cases, the detectable label may be a part of a binding pair, which can then be subsequently detected. Signals from the detectable label may be detected by various means and will depend on the nature of the detectable label. Examples of means to detect detectable label include but are not limited to spectroscopic, photochemical, biochemical, immunochemical, electromagnetic, radiochemical, or chemical means, such as fluorescence, chemifluoresence, or chemiluminescence, or any other appropriate means.

A "fragment" in the context of a gene fragment or a chromosome fragment refers to a sequence of nucleotide residues which are at least about 10 nucleotides, at least about 20 nucleotides, at least about 25 nucleotides, at least about 30 nucleotides, at least about 40 nucleotides, at least about 50 nucleotides, at least about 100 nucleotides, at least about 250 nucleotides, at least about 500 nucleotides, at least about 1,000 nucleotides, at least about 2,000 nucleotides, at least about 5,000 nucleotides, at least about 10,000 nucleotides, at least about 20,000 nucleotides, at least about 50,000 nucleotides, at least about 100,000 nucleotides, at least about 500,000 nucleotides, at least about 1,000,000 nucleotides or more.

The term "genetic abnormality" or "chromosomal abnormality" as used herein refers to a deviation of the nucleic acid sequence from a wild-type or normal genetic sequence. A genetic abnormality may reflect a difference between the full genetic complement of an organism, or any portion thereof, as compared to a normal full genetic complement of all chromosomes in that organism. For example, a genetic abnormality may include a change in chromosomes or a portion thereof (e.g., deletions, duplications, amplifications); or a change in chromosomal structure (e.g., translocations, point mutations). Genetic abnormality may be hereditary, i.e., passed from generation to generation or non-hereditary. Genetic abnormalities may be present in some cells of an organism or in all cells of that organism.

The term "endogenous control gene" as used herein refers to genes that are generally always expressed and thought to be involved in routine cellular metabolism. Endogenous control genes are well known and include such genes as ABL, glyceraldehyde-3-phosphate dehydrogenase (G3PDH or GAPDH), albumin, actins, tubulins, cyclophilin, hypoxanthine phosphoribosyltransferase (HRPT), L32, 28S, and 18S rRNAs. Detection of endogenous control genes in a diagnostic assay may serve as a positive control for the assay.

The terms "identity" and "identical" refer to a degree of identity between sequences, there may be partial identity or complete identity. A partially identical sequence is one that is less than 100% identical to another sequence. Partially identical sequences may have an overall identity of at least 70% or at least 75%, at least 80% or at least 85%, or at least 90% or at least 95%.

As used herein, the terms "isolated", "purified" or "substantially purified" refer to molecules, such as nucleic acid, that are removed from their natural environment, isolated or separated, and are at least 60% free, preferably 75% free, and most preferably 90% free from other components with which they are naturally associated. An isolated molecule is therefore a substantially purified molecule.

The term "multiplex PCR" as used herein refers to an assay that provides for simultaneous amplification and detection of two or more products within the same reaction vessel. Each product is primed using a distinct primer pair. A multiplex reaction may further include specific probes for each product that are detectably labeled with different detectable molecules.

As used herein, the term "oligonucleotide" refers to a short polymer composed of deoxyribonucleotides, ribonucleotides or any combination thereof. Oligonucleotides are generally between about 10, 11, 12, 13, 14, 15, 20, 25, or 30 to about 150 nucleotides (nt) in length, more preferably about 10, 11, 12, 13, 14, 15, 20, 25, or 30 to about 70 nt, and most preferably between about 18 to about 26 nt in length.

As used herein, a "primer" is an oligonucleotide that is complementary to a target nucleotide sequence and leads to addition of nucleotides to the 3' end of the primer in the presence of a DNA or RNA polymerase. The 3' nucleotide of the primer should generally be identical to the target sequence at a corresponding nucleotide position for optimal extension and/or amplification. The term "primer" includes all forms of primers that may be synthesized including peptide nucleic acid primers, locked nucleic acid primers, phosphorothioate modified primers, labeled primers, and the like. As used herein, a "forward primer" is a primer that is complementary to the anti-sense strand of dsDNA. A "reverse primer" is complementary to the sense-strand of dsDNA. As used herein, a "5' target primer pair" is at least one forward primer and at least one reverse primer that amplifies the 5' region of a target nucleotide sequence. As used herein, a "3' target primer pair" is at least one forward primer and at least one reverse primer that amplifies the 3' region of a target nucleotide sequence.

An oligonucleotide (e.g., a probe or a primer) that is specific for a target nucleic acid will "hybridize" to the target nucleic acid under suitable conditions. As used herein, "hybridization" or "hybridizing" refers to the process by which an oligonucleotide single strand anneals with a complementary strand through base pairing under defined hybridization conditions. It is a specific, i.e., non-random, interaction between two complementary polynucleotides. Hybridization and the strength of hybridization (i.e., the strength of the association between the nucleic acids) is influenced by such factors as the degree of complementary between the nucleic acids, stringency of the conditions involved, and the $T_m$ of the formed hybrid.

"Specific hybridization" is an indication that two nucleic acid sequences share a high degree of complementarity. Specific hybridization complexes form under permissive annealing conditions and remain hybridized after any subsequent washing steps. Permissive conditions for annealing of nucleic acid sequences are routinely determinable by one of ordinary skill in the art and may occur, for example, at 65° C. in the presence of about 6×SSC. Stringency of hybridization may be expressed, in part, with reference to the temperature under which the wash steps are carried out. Such temperatures are typically selected to be about 5° C. to 20° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. Equations for calculating $T_m$ and conditions for nucleic acid hybridization are known in the art.

As used herein, an oligonucleotide is "specific" for a nucleic acid if the oligonucleotide has at least 50% sequence identity with a portion of the nucleic acid when the oligonucleotide and the nucleic acid are aligned. An oligonucleotide that is specific for a nucleic acid is one that, under the appropriate hybridization or washing conditions, is capable of hybridizing to the target of interest and not substantially hybridizing to nucleic acids which are not of interest. Higher levels of sequence identity are preferred and include at least 75%, at least 80%, at least 85%, at least 90%, at least 95% and more preferably at least 98% sequence identity. Sequence identity can be determined using a commercially available computer program with a default setting that employs algorithms well known in the art BLAST). As used herein, sequences that have "high sequence identity" have identical nucleotides at least at about 50% of aligned nucleotide positions, preferably at least at about 60% of aligned nucleotide positions, and more preferably at least at about 75% of aligned nucleotide positions.

The terms "target nucleic acid," "target gene" and "target sequence" are used interchangeably herein and refer to nucleic acid sequence which is intended to be identified. Target nucleic acids may include 5' or 3' regions of a target gene or any other sequence of interest. Target nucleic acids may represent alternative sequences or alleles of a particular gene. Target nucleic acids can be double stranded or single stranded, or partially double stranded, or partially single stranded or a hairpin molecule. Target nucleic acids can be about 1-5 bases, about 10 bases, about 20 bases, about 50 bases, about 100 bases, about 500 bases, about 1,000 bases, about 2,000 bases, 2,500 bases, about 3,000 bases, about 3,000 bases, about 4,000 bases, about 5,000 bases, about 7,500 bases, about 10,000 buses, about 20,000 bases, about 30,000 bases, about 40,000 bases, about 50,000 bases, about 75,000 bases, about 100,000 bases, about 1,000,000 bases or more.

The term "transcript," when referring to a target nucleic acid, refers to any nucleic acid that is representative of the genomic nucleic acid of a cell including, for example. RNA in any form (e.g., mRNA, pre-mRNA, and snRNA) and synthetic representations of such as cDNA.

The term "test sample" as used herein refers to a sample, which contains nucleic acid or is suspected of containing nucleic acid. In some embodiments, the nucleic acids in the test sample are for use in accordance with the methods disclosed herein. In some embodiments, a test sample is a biological sample.

The term "biological sample" as used herein refers to a sample, which contains target nucleic acids or be used as a source of target nucleic acids for the methods of the invention. A biological sample may include clinical samples (i.e., obtained directly from a patient) or isolated nucleic acids and may be cellular or acellular fluids and/or tissue (e.g., biopsy) samples. In some embodiments, a sample is obtained from a tissue or bodily fluid collected from a subject. Sample sources include, but are not limited to, sputum (processed or unprocessed), bronchial alveolar lavage (BAL), bronchial wash (BW), whole blood or isolated blood cells of any type (e.g., lymphocytes), bodily fluids, cerebrospinal fluid (CSF), urine, plasma, serum, or tissue (e.g., biopsy material). The term "patient sample" as used herein refers to a sample obtained from a human seeking diagnosis and/or treatment of a disease. In the case where the subject is a fetus, the patient sample can be from the subject (i.e., fetus), amniotic fluid, or maternal (e.g. the mother's blood).

As used herein, the term "subject" refers to a mammal, such as a human, but can also be another animal such as a domestic animal (e.g., a dog, cat, or the like), a farm animal (e.g., a cow, a sheep, a pig, a horse, or the like) or a laboratory animal (e.g., a monkey, a rat, a mouse, a rabbit, a guinea pig, or the like). The term "patient" refers to a "subject" who is, or is suspected to be, afflicted with disease related to a chromosomal abnormality.

General Overview of the Technology

Disclosed herein are methods for detecting the presence or absence of target gene dysregulations in subjects based, at least in part, on results of the testing methods of the present technology on a sample. The test samples disclosed herein are represented by, but not limited in any way to, e.g., blood (or a fraction of blood such as plasma, serum, or particular cell fractions), lymph, mucus, tears, saliva, cystic fluid, urine, semen, stool, CSF, ascites fluid, whole blood, and biopsy samples of body tissue, fine needle aspirate (FNA), bronchalvcolar lavage (BAL). This disclosure is also drawn, inter alia, to methods of diagnosing or monitoring cancer. The cancer can be lung or prostate cancer bone and soft tissue sarcomas, various leukemias and lymphomas.

The technology generally provides for the detection, measuring, and comparison of gene expression of different regions of a target gene within a test sample. Accordingly, the various aspects relate to the collection, preparation, separation, identification, characterization, and comparison of the abundance of messenger RNA in a test sample. The technology further relates to detecting and/or monitoring a sample containing a messenger RNA for a 5' region of a target gene and a 3' region of a target gene. As used herein, the phrases "detecting the amount" or "detecting the level" refer to the quantity of transcript from any gene or part of a gene, such as the 5' region of a gene, a 3' region of the target gene, a reference gene. The amount can be expressed as a concentration, as a number of copies, or as a Ct value, for example. The threshold cycle, or Ct, value is the cycle at which signal intersects a threshold value when performing real-time nucleic acid amplification.

Specimens that do not contain a chromosomal abnormality within a target gene will demonstrate the same expression pattern, between the 5' region and the 3' region because they are linked in a unimolecular fashion. However, when the target gene is affected by some genetic or chromosomal abnormality, the 5' and 3' regions may show independent expression patterns for the 5' and 3' regions. In the case of a translocation, the 5' and 3' regions will show different expression patterns because these two regions are now unlinked on the chromosome.

More specifically, a gene that undergoes certain rearrangements will exhibit differential expression of the 5' region relative to the 3' region. This occurs in situations where the 5' region of a gene remains under the control of the gene's regulatory elements, e.g., those elements contained in the 5' untranslated region (UTR). The 3' region of the gene is juxtaposed so as to be under the control of different regulatory elements or none at all. For these types of mutations, the 5' region of the gene (e.g., at least one sequence that is specific to the 5' region such that it occurs upstream of the mutation break point or deletion site) is expressed according to the target gene's own regulatory elements, while the 3' region (e.g., at least one sequence that is specific to the 3' region of the gene that occurs downstream of the mutation break point or deletion site) will not be expressed, in the case where the 3' region is deleted, or translocated to a position that is not actively expressed, or expressed at a level consistent with the regulatory elements of a different gene.

Thus, the methods provide for detecting these mutations that result in the differential expression of the 5' region of a gene relative to the 3' region of the gene. One example of this situation occurs in many prostate cancer patients, who have a translocation of the TMPRSS2 gene such that the 5' region of the TMPRSS2 gene remains under the control of the robust TMPRSS2 promoter, and the 3' region of the TMPRSS2 gene is translocated such that it is expressed by the less robust ERG or ETV promoter.

As used herein, the phrases "difference of the level" and "difference in amounts" refer to differences in the quantity of transcript from the 5' region of a gene compared to the quantity of transcript from the 3' region of the target gene. In one embodiment, a transcript from the 5' region of a gene is present at an elevated amount or at a decreased amount in a sample compared to the amount of transcript from the 3' region of the target gene. In wild-type or normal cells, the quantity of transcript of the 5' region of the target gene and the quantity of transcript from the 3' region of the target gene is expected to be at equal or near-equal quantities. By equal quantity, it is meant that the measured amounts of transcript or detectable signal (which correlates to the amount of transcript) for the 5' region and the 3' region do not exhibit a statistically significant difference from the same comparison in control samples. Methods for comparing these values are known to those of skill in the art and include, but are not limited to, a Student's t-test and ANOVA analysis. The artisan recognizes that, because of technical differences inherent in the detection methodologies used herein, the amount of detectable signal from the 5'-region may not necessarily be equal to the amount of detectable signal from the 3'-region even though no chromosomal abnormality is present (i.e., both regions remain linked in a unimolecular manner and under the control of the same regulatory elements).

Distinct 3'-target gene expression levels expected to be found in samples containing target gene translocations and those without translocations can be established by normalizing the expression levels of 3' target gene to 5' target gene. An IDE Score can be calculated according to the following formula:

$$\text{IDE Score} = 2^{-(Ct_{3'\text{-target gene}}) - (Ct_{5'\text{-target gene}})}$$

wherein the Ct (threshold cycle) values can be obtained by RT-PCR.

In other embodiments, the 3'- and 5'-target gene measurements may be normalized to an endogenous control gene when calculating an IDE score. Some useful formulae include, for example:

(3' Target)/(Control)−(5' Target)/(Control), or (3' Target)/(5' Target), or

Ln((3'Target)/(Control))−Ln((5'Target)/(Control))

In other embodiments, the measured amount of the 3'- and 5'-transcripts in the test sample may be normalized to the level of the same transcripts from a control sample, rather than an endogenous gene.

In some embodiments, if the mean amount of transcript or detectable signal for the 5' region and the 3' region are within about 1 standard deviation, within about 0.5 standard deviations, within about 0.2 standard deviations, within about 0.1 standard deviations, or within about 0.01 standard deviations, then there may be no significant difference between the two amounts. In this example, one could conclude that the 5' and 3' regions are expressed in a unimolecular fashion and there is no chromosomal abnormality in the target gene.

On the other hand, if the mean amount of transcript or detectable signal for the 5' region and the 3' region exceed about 1 standard deviation, about 1.5 standard deviations, about 2.0 standard deviations, or about 2.5 stand deviations, then there may be a significant difference between the two amounts. In this example, one could conclude that the 5' and 3' regions are expressed under the control of different promoters (or one region may not be expressed at all), such that there is a chromosomal abnormality in the target gene.

The measured amounts of transcript or detectable signal (which correlates to the amount of transcript) may be expressed as a "relative amount" or "ratio" of the expression of the 5' region of the target gene relative to the 3' region of the target gene. Relative amounts may be a single value or a range of values. For example, a range of values may be used to generate a standard curve relationship between the relative amount of detectable signal formed versus some other quantity (e.g., number of mRNA molecules). If the ratio of the expression of the 5' region of the target gene relative to the expression of the 3' region of the target gene is statistically less than or greater than 1, then a chromosomal abnormality is detected. Where the ratio is less than 1, the 3' region of the target gene has been translocated to a genomic region that is more transcriptionally active than the native target gene. Where the ratio is greater than 1, the 3' region has either been deleted or translocated to a genomic region that is less transcriptionally active than the native target gene.

In some embodiments, a sample obtained from a subject is assayed to determine the relative expression levels of the 5' and 3' regions of a particular gene or nucleic acid sequence of interest. Real-time RT-PCR (real-time reverse transcript-polymerase chain reaction) is a sensitive technique for mRNA detection and quantitation. Compared to the two other commonly used techniques for quantifying mRNA levels, Northern blot analysis and RNase protection assays, RT-PCR can be used to quantify mRNA levels from much smaller samples. In fact, this technique is sensitive enough to enable quantitation of RNA from a single cell.

One of skill in the art would know how to design oligonucleotide primers and probes that are used to detect differential 5' and 3' expression from any gene of interest, provided the sequence of the gene of interest is known. The size of the primer will depend on many factors, including the ultimate function or use of the oligonucleotide. An oligonucleotide that functions as an extension primer or probe, for example, will be sufficiently long to prime the synthesis of extension products in the presence of a catalyst, e.g., DNA polymerase, and deoxynucleotide triphosphates.

Alternatively, an insertion or transposition event can lead to the differential expression of the 5' region and the 3' region of a target gene. The insertion of, for example, a promoter or other regulatory element, or the transposition of a transposable element into the middle of the coding sequence of a gene of interest can create a situation where the 5' region of the target gene is expressed at a different level than the 3' region of the target gene.

Any such mutation that results in the differential expression of a 5' region of a target gene and the 3' region of the target gene is detectable according to the methods, compositions and kits described herein. One of skill in the art would know how to directed, for example, RT-PCR primers to a 5' region of a gene of interest that occurs at or near the start of transcription, thereby ensuring a product corresponding to a 5' region that occurs downstream of a potential chromosomal abnormality. One of skill in the art need only refer to the known sequence of the target gene and known base-pairing rules to determine an effective RT-PCR primer or primer pair. Likewise, one of skill in the art could design a primer or primer pair directed to a 3' region of the gene of interest. In particular examples, where a known chromosomal abnormality occurs, one of skill in the art is further aided by the knowledge of a known mutation site, thereby allowing the design of primers that are at or near the mutation site, e.g., a primer or primer pair could be designed immediately 5' of the mutation site and immediately 3' of the mutation site; or the primer or primer pairs could be designed, for example, within about 5 nucleotides (nt) of the mutation site on either side, within about 10 nt of the mutation site on either side, within about 20 nt of the mutation site on either side, within about 50 nt of the mutation site on either side, within about 100 nt of the mutation site on either side, within about 250 nt of the mutation site on either side or within about 500 nt of the mutation site on either side.

Chromosomal Abnormality: Types and Associated Diseases

A chromosomal abnormality may reflect a difference between the full genetic complement or any portion thereof, of an organism, as compared to a normal full genetic complement of all chromosomes in that organism. For example, a genetic abnormality may include a change in chromosomal copy number (e.g., aneuploidy), or a portion thereof (e.g., deletions, duplications, amplifications); or a change in chromosomal structure (e.g., translocations, point mutations). A genetic abnormality may lead to pathological conditions. While some diseases, such as cancer, are due to chromosomal abnormalities acquired in a few cells during life, the term "genetic disease" most commonly refers to diseases present in all cells of the body and present since conception. Genetic abnormalities may be hereditary or non-hereditary.

Genetic duplication is any duplication of a region of the genomic sequence. It may occur as an error in homologous recombination, a retrotransposition event, or duplication of an entire chromosome. Duplication of a gene has been associated with several diseases such as some cases of pagetic osteosarcoma is associated with duplication of MYC gene (*Sarcoma*, 1(3-4):131-134, 1997), some cases of breast cancer are associated with duplication of HER-2/neu gene (*Ann Oncol.*, 12(suppl 1):S3-S8, 2001), some cases of bladder tumor are associated with duplication of c-erb-2 gene (*Cancer Res.*, 55:2422-2430, 1995).

A deletion (also called gene deletion, deficiency, or deletion mutation) is a genetic aberration in which a part of a chromosome or a sequence of DNA is missing. Deletion is the loss of genetic material. Any number of nucleotides can be deleted, from a single base to an entire piece of chromosome. Deletions can be caused by errors in chromosomal crossover during meiosis. Deletions are associated with an array of genetic disorders, including some cases of male infertility and two thirds of cases of Duchenne muscular dystrophy, a deletion of part of the short arm of chromosome 5 results in a syndrome called Cri du chat, also known as "cry of the cat" syndrome.

A chromosome "translocation" is the interchange of parts between nonhomologous chromosomes. It is generally detected through cytogenetics or a karyotyping of affected cells. There are two main types, reciprocal, in which all of the chromosomal material is retained and Robertsonian, in which some of the chromosomal material is lost. Further, translocations can be balanced (in an even exchange of material with no genetic information extra or missing) or unbalanced (where the exchange of chromosome material is unequal resulting in extra or missing genes).

A reciprocal translocation between chromosomes 9 and 22 resulting in a cytogenetically distinct acrocentric chromosome termed the Philadelphia chromosome. This translocation fuses the BCR gene locus of chromosome 22 and the proto-oncogene ABL locus of chromosome 9 to form a her/abl oncogenic protein (Tefferi et al. *Mava Clin Proc.* 80(3):390-402, 2005). Although the Philadelphia chromosome was first associated with CML, it is now known to be an indicator of prognosis in other blood disorders such as acute lymphoblastic leukemia (ALL).

Translocations have been linked with other diseases. For example, the fusion of the CBP gene of chromosome 16 to the MLL gene of chromosome 11 through a translocation between chromosomes 11 and 16 has been associated with leukemia (Zhang et al., *Genes Chromosomes Cancer*, 41(3): 257-65, 2004). Similarly, a translocation between chromosomes 8 and 21, resulting in a fusion of the AML1 and ETO genes is involved in nearly 15% of acute myeloid leukemia (AML) cases (Zhang et al., *Science*, 305:1286-9, 2004). Further, a number of chromosomal translocations have been identified in various forms of lymphoma. For example, a translocation between chromosomes 8 and 14 involving the c-myc gene is reported to be present in approximately 80-85% of Burkitt lymphoma/leukemia cases (Vega et al., *Arch Pathol Lab Med*, 127:1148-1160, 2003). A further example is a translocation that results in the fusion of the EML4 gene and ALK gene. This EML4-ALK fusion translocation has been associated with NSCLC (Permer, et al., *Neoplasia*, 10(3):298-302, 2008). Exemplary EML4:ALK fusions include the chromosome 2p inversion (inv(2)(p21: p23)) which has been identified in 3-7% of all NSCLCs and the at least 11 identified variants of EML4:ALK translocations. In certain embodiments, IDE methods disclosed herein allow for detection of translocations irrespective of the chromosomal breakpoint.

In another example, a fusion of the androgen-regulated gene TMPRSS2 and members of the ETS family of transcription factors (e.g., ERG, ETV1, and ETV4) have been identified in prostate cancers. Recurrent gene fusions of the 5' untranslated region of TMPRSS2 to ERG or ETV1 were found in prostate cancer tissues with outlier expression (Tomlins, S. et al., *Science*, 310:644-648, 2005). These gene fusions occur in the majority of prostate cancers identified by PSA screening and are the driving mechanism for over-expression of the three members of the ETS transcription factor family, either ERG (21q22.3), ETV1 (7p21.2), or ETV4 (17q21). It was found that 23 of 29 prostate cancer samples harbored rearrangements in ERG or ETV1. Cell line experiments suggested that the androgen-responsive promoter elements of TMPRSS2 mediate the overexpression of ETS family members in prostate cancer. Considering the high incidence of prostate cancer and the high frequency of this gene fusion, the TMPRSS2-ETS gene fusion is the most common genetic aberration so far described in human malignancies. ERG is the most common fusion partner of the ETS genes with TMPRSS2. This gene fusion is considered to be an early event in prostate cancer development. Fusion status in prostate cancer may determine clinical outcome. The methods, compositions and kits described herein, therefore, are useful for the detection of TMPRSS2 translocations that are prevalent in prostate cancer patients, thereby allowing to the detection of prostate cancer or an individual who is at risk for developing prostate cancer.

Genetic abnormalities may also be point mutations insertions, or deletions. A point mutation, or substitution, is a type of mutation that causes the replacement of single base nucleotide with another nucleotide. Insertion and deletion includes insertions or deletions of a single base pair. Mutations in the gene or chromosome often are associated with diseases such as sickle cell anemia, cystic fibrosis, hemophilia, phenylketonuria, spina bifida, etc.

Target Nucleic Acids and Primers

The methods of the present invention relate to the detection of chromosomal abnormalities in a target gene by amplifying a 5' region of the target gene transcript, if present, in a biological sample with one or more 5' target primer pairs which are complementary to the 5' region of the target gene; and amplifying a 3' region of the target gene transcript, if present, in the biological sample with one or more 3' target primer pairs which are complementary to the 3' region of the target gene. Such regions can be amplified and isolated by PCR using oligonucleotide primers designed based on genomic and/or cDNA sequences that encompass the regions. Any target gene that is potentially affected by chromosomal abnormalities could be assayed according to the methods described herein.

The term "5' region" refers to the portion of a polynucleotide located towards the 5' end of the polynucleotide relative to the 3' region, and may or may not include the 5' most nucleotide(s) of the same polynucleotide. In the context of translocations, the 5'-region refers to a region that is in the 5' direction or upstream of a translocation breakpoint. In the context of the present methods, the 5' region may be located near the 5' end of the transcribed portion of the target gene. In some embodiments, the 5' region encompasses all or a portion of the 5' untranslated region (UTR) of the target gene. In other embodiments, the 5' region is located downstream of the start codon (if the target gene is a protein-coding gene); for example, at least 10, at least 50, at least 100, at least 200, or at least 500 nucleotides downstream of the stop codon. The sue of the 5' region to be amplified can vary depending on the detection method chosen. In some embodiments, the primers may be selected to amplify at least 10, at least 20, at least 30, at least 50, at least 100, at least 200, or at least 500 nucleotides in the 5' region.

The term "3' region" refers to the portion of a polynucleotide located towards the 3' end of the polynucleotide relative to the 5' region, and may or may not include the 3' most nucleotide(s) of the same polynucleotide. In the context of translocations, the 3'-region refers to a region that is in the 3' direction or downstream of a translocation breakpoint. In the context of the present methods, the 3' region may be located near the 3' end of the transcribed portion of the target gene. In some embodiments, the 3' region encompasses all or a portion of the 3' UTR of the target gene. In other embodiments, the 3' region is located upstream of the stop codon (if the target gene is a protein-coding gene); for example, at least 10, at least 50, at least 100, at least 200, or at least 500 nucleotides upstream of the stop codon. The size of the 3' region to be amplified can vary depending on the detection method chosen. In some embodiments, the primers may be selected to amplify at least 10, at least 20, at least 30, at least 50, at least 100, at least 200, or at least 500 nucleotides in the 3' region.

When assessing known genetic abnormalities, the terms "5'-region" and "3'-region" are somewhat relative in that each region is selected to be on a different side of the detect (e.g., breakpoint) that results in the genetic abnormality. These regions may be selected for convenience or other substantive reasons (i.e., simultaneous assessment of other abnormalities such as mutations (SNPs), deletions, insertions, and the like) and need not be at the 5'- and 3'-termini, respectively, of the transcript. It is preferable that, when assessing target nucleic acids for unknown transcripts (i.e., a specific breakpoint has not been previously identified), the distance between the 5' region and the 3' region for a particular target gene should be maximized to the greatest extent possible to allow for the detection of a variety of chromosomal abnormalities that may occur between the two regions. This strategy maximizes the possibility that any breakpoint associated with a genetic abnormality occur between the two regions. In one embodiment, one or both of the 5'- and 3'-regions assessed by the methods of this invention are located in the untranslated regions (UTRs) of the transcripts. Guidelines for selecting primers for PCR amplification are well known in the art. See. e.g., McPherson et al., PCR Basics: From Background to Bench, Springer-Verlag, 2000. A variety of computer programs for designing primers are available, e.g., Oligo (National Biosciences. Inc. Plymouth Minn.), MacVector (Kodak/IBI), and the GCG suite of sequence analysis programs (Genetics Computer Group, Madison, Wis. 53711).

Sample Preparation

Specimens from which target nucleic acids can be detected and quantified with the methods of the present invention may be obtained from subjects according to methods known to those of skill in the art. Specimens may be taken from body tissue and fluids such as blood (including whole blood, serum, and plasma), urine, cerebrospinal fluid (CSF), synovial fluid, pleural fluid, pericardial fluid, intraocular fluid, tissue biopsies or endotracheal aspirates, sputum, stool, swabs from, e.g., skin, inguinal, nasal and/or throat. Methods of obtaining test samples and reference samples are well known to those of skill in the art and include, but are not limited to, aspirations, tissue sections, drawing of blood or other fluids, surgical or needle biopsies, collection of paraffin embedded tissue, collection of body fluids, collection of stool, and the like. In one embodiment, the test sample may be obtained from an individual who is suspected of having a disease or a genetic abnormality. In some embodiments, specimens are tissue samples (biopsy samples) from a subject having or suspected of having a disease or a genetic abnormality.

The nucleic acid (DNA and/or RNA) may be isolated from the sample according to any methods well known to those of skill in the art. If necessary, the sample may be collected or concentrated by centrifugation and the like. The cells of the sample may be subjected to lysis, such as by treatments with enzymes, heat surfactants, ultrasonication or combinations thereof. The lysis treatment is performed in order to obtain a sufficient amount of RNA derived from the cells of interest, if present in the sample, to detect using RT-PCR. Nucleic acid need not be extracted, but may be made available by suitable treatment of cells or tissue such as described in US Patent Publication No. 2008/131876.

In one embodiment, mRNA or cDNA generated from mRNA or total RNA may be used. Various methods of RNA extraction are suitable for isolating the RNA. Suitable methods include phenol and chloroform extraction. See Maniatis et al., *Molecular Cloning, A Laboratory Manual*, 2d, Cold Spring Harbor Laboratory Press, page 16.54 (1989). In addition kits for isolating mRNA and synthesizing cDNA are commercially available e.g., RNeasy Protect Mini kit, RNeasy Protect Cell Mini kit from Qiagen.

In one embodiment, a dual RNA/DNA isolation method is used employing a trizol based reagent for initial isolation of RNA and DNA from patient samples. Upon contact with patient samples, the phenol and high salt reagents in the trizol effectively inactivate any disease agent or secondary disease agent that may be present in the patient sample. After the RNA and DNA are isolated from the patient samples, a silica based column may be used to further isolate the RNA and DNA. The use of silica based columns allows for wash steps to be performed quickly and efficiently while minimizing the possibility of contamination. The wash steps may be used to remove PCR and RT-PCR inhibitors. The column method for nucleic acid purification is advantageous as it can be used with different types of patient samples and the spin and wash steps effectively remove PCR or RT-PCR inhibitors.

Amplification of Nucleic Acids

Nucleic acid samples or target nucleic acids may be amplified by various methods known to the skilled artisan. In suitable embodiments, PCR is used to amplify nucleic acids of interest. Briefly, in PCR, two primer sequences are prepared that are complementary to regions on opposite complementary strands of the marker sequence. An excess of deoxynucleotide triphosphates are added to a reaction mixture along with a DNA polymerase, e.g., Taq polymerase.

In one embodiment, the target nucleic acids are amplified in a multiplex amplification reaction. A variety of multiplex amplification strategies are known in the art and may be used with the methods of the invention. The multiplex amplification strategy may use PCR, RT-PCR or a combination thereof depending on the type of nucleic acid contained in the disease agent(s). For example, if an RNA genome is present, RT-PCR may be utilized. The PCR enzyme may be an enzyme with both a reverse transcription and polymerase function. Furthermore, the PCR enzyme may be capable of "hot start" reactions as is known in the art.

If the target sequence is present in a sample, the primers will bind to the sequence and the polymerase will cause the primers to be extended along the target sequence by adding on nucleotides. By raising and lowering the temperature of the reaction mixture, the extended primers will dissociate from the target nucleic acid to form reaction products, excess primers will bind to the target nucleic acid and to the reaction products and the process is repeated, thereby generating amplification products. Cycling parameters can be varied, depending on the length of the amplification products to be extended. An internal positive amplification control (IC) can be included in the sample, utilizing oligonucleotide primers and/or probes.

Detection of Amplified Nucleic Acids

Amplification of nucleic acids can be detected by any of a number of methods well-known in the art such as gel electrophoresis, column chromatography, hybridization with a probe, sequencing, melting curve analysis, or "real-time" detection.

In one approach, sequences from two or more fragments of interest are amplified in the same reaction vessel (i.e., "multiplex PCR"). Detection can take place by measuring the end-point of the reaction or in "real time." For real-time detection, primers and/or probes may be detectably labeled to allow differences in fluorescence when the primers become incorporated or when the probes are hybridized, for example, and amplified in an instrument capable of monitoring the change in fluorescence during the reaction. Real-time detection methods for nucleic acid amplification are well known and include, for example, the TaqMan® system, the Scorpion™ bi-functional molecule, and the use of intercalating dyes for double stranded nucleic acid.

In end-point detection, the amplicon(s) could be detected by first size-separating the amplicons, then detecting the size-separated amplicons. The separation of amplicons of different sizes can be accomplished by, for example, gel electrophoresis, column chromatography, or capillary electrophoresis. These and other separation methods are well-known in the art. In one example, amplicons of about 10 to about 150 base pairs whose sizes differ by 10 or more base pairs can be separated, for example, on a 4% to 5% agarose gel (a 2% to 3% agarose gel for about 150 to about 300 base pair amplicons), or a 6% to 10% polyacrylamide gel. The separated nucleic acids can then be stained with a dye such as ethidium bromide and the size of the resulting stained band or bands can be compared to a standard DNA ladder.

In another embodiment, two or more fragments of interest are amplified in separate reaction vessels. If the amplification is specific, that is, one primer pair amplifies for one fragment of interest but not the other, detection of amplification is sufficient to distinguish between the two types— size separation would not be required.

In some embodiments, amplified nucleic acids are detected by hybridization with a specific probe. Probe oligonucleotides, complementary to a portion of the amplified target sequence may be used to detect amplified fragments. Hybridization may be detected in real time or in non-real time. Amplified nucleic acids for each of the target sequences may be detected simultaneously (i.e., in the same reaction vessel) or individually (i.e., in separate reaction vessels). In some embodiments, the amplified DNA is detected simultaneously, using two or more distinguishably-labeled, gene-specific oligonucleotide probes, one which hybridizes to the first target sequence and one which hybridizes to the second target sequence.

The probe may be detectably labeled by methods known in the art. Useful labels include, e.g., fluorescent dyes (e.g., Cy5®, Cy3®, FITC, rhodamine, lanthamide phosphors, Texas red, FAM, JOE, Cal Fluor Red 610®, Quasar 670®). $^{32}P$, $^{35}S$, $^{1}H$, $^{14}C$, $^{125}I$, $^{131}I$, electron-dense reagents (e.g., gold), enzymes, e.g., as commonly used in an ELISA (e.g., horseradish peroxidase, beta-galactosidase, luciferase, alkaline phosphatase), colorimetric labels (e.g., colloidal gold), magnetic labels (e.g., Dynabeads™), biotin, dioxigenin, or haptens and proteins for which antisera or monoclonal antibodies are available. Other labels include ligands or oligonucleotides capable of forming a complex with the corresponding receptor or oligonucleotide complement, respectively. The label can be directly incorporated into the nucleic acid to be detected, or it can be attached to a probe (e.g., an oligonucleotide) that hybridizes or binds to the nucleic acid to be detected.

One general method for real time PCR uses fluorescent probes such as the TaqMan® probes, molecular beacons, and Scorpions™, Real-time PCR quantitates the initial amount of the template with more specificity, sensitivity and reproducibility, than other forms of quantitative PCR, which detect the amount of final amplified product. Real-time PCR does not detect the size of the amplicon. The probes employed in Scorpion™ and TaqMan® technologies are based on the principle of fluorescence quenching and involve a donor fluorophore and a quenching moiety.

In one embodiment, the detectable label is a fluorophore. The term "fluorophore" as used herein refers to a molecule that absorbs light at a particular wavelength (excitation frequency) and subsequently emits light of a longer wavelength (emission frequency). The term "donor fluorophore" as used herein means a fluorophore that, when in close proximity to a quencher moiety, donates or transfers emission energy to the quencher. As a result of donating energy to the quencher moiety, the donor fluorophore will itself emit less light at a particular emission frequency that it would have in the absence of a closely positioned quencher moiety.

The term "quencher moiety" as used herein means a molecule that, in close proximity to a donor fluorophore, takes up emission energy generated by the donor and other dissipates the energy as heat or emits light of a longer wavelength than the emission wavelength of the donor. In the latter case, the quencher is considered to be an acceptor fluorophore. The quenching moiety can act via proximal (i.e., collisional) quenching or by Förster or fluorescence resonance energy transfer ("FRET"). Quenching by FRET is generally used in TaqMan® probes while proximal quenching is used in molecular beacon and Scorpion™ type probes.

In proximal quenching (a.k.a. "contact" or "collisional" quenching), the donor is in close proximity to the quencher moiety such that energy of the donor is transferred to the quencher, which dissipates the energy as heat as opposed to a fluorescence emission. In FRET quenching, the donor fluorophore transfers its energy to a quencher which releases the energy as fluorescence at a higher wavelength. Proximal quenching requires very close positioning of the donor and quencher moiety, while FRET quenching, also distance related, occurs over a greater distance (generally 1-10 nm, the energy transfer depending on R-6, where R is the distance between the donor and the acceptor). Thus, when FRET quenching is involved, the quenching moiety is an acceptor fluorophore that has an excitation frequency spectrum that overlaps with the donor emission frequency spectrum. When quenching by FRET is employed, the assay may detect an increase in donor fluorophore fluorescence resulting from increased distance between the donor and the quencher (acceptor fluorophore) or a decrease in acceptor fluorophore emission resulting from decreased distance between the donor and the quencher (acceptor fluorophore).

Suitable fluorescent moieties include the following fluorophores known in the art: 4-acetamido-4'-isothiocyanatostilbene-2,2'disulfonic acid, acridine and derivatives (acridine, acridine isothiocyanate) Alexa Fluor® 350, Alexa Fluor® 488, Alexa Fluor® 546, Alexa Fluor® 555, Alexa Fluor® 568, Alexa Fluor® 594, Alexa Fluor® 647 (Molecular Probes), 5-(2'-aminoethyl)aminonaphthalene-1-sulfonic acid (EDANS), 4-amino-N-[3-vinylsulfonyl)phenyl]naphthalimide-3,5 disulfonate (Lucifer Yellow VS), N-(4-anilino-1-naphthyl)maleimide, anthranilamide, Black Hole Quencher (BHQ™) dyes (Biosearch Technologies), BODIPY® R-6G, BODIPY® 530/550, BODIPY® FL, Brilliant Yellow, coumarin and derivatives (coumarin, 7-amino-4-methylcoumarin (AMC, Coumarin 120), 7-amino-4-trifluoromethylcouluarin (Coumarin 151)), Cy2®, Cy3®, Cy3.5®, Cy5®, Cy5.5®, cyanosine, 4',6-diaminidino-2-phenylindole (DAPI), 5',5"-dibromopyrogallol-sulfonephthalem (Bromopyrogallol Red), 7-diethylamino-3-(4'-isothiocyanatophenyl)-4-methylcoumarin, diethylenetriamine pentaacetate, 4,4'-diisothiocyanatodihydro-stilbene-2,2'-disulfonic acid, 4,4'-diisothiocyanatostilbene-2,2'-disulfonic acid, 5-[dimethylamino]naphthalene-1-sulfonyl chloride (DNS, dansyl chloride), 4-(4'-dimethylaminophenylazo)benzoic acid (DABCYL), 4-dimethylaminophenylazophenyl-4'-isothiocyanate (DABITC), Eclipse (Epoch Biosciences Inc.), eosin and derivatives (eosin, eosin isothiocyanate), erythrosin and derivatives (erythrosin B, erythrosin isothiocyanate), ethidium, fluorescein and derivatives (5-carboxyfluorescein (FAM), 5-(4,6-dichlorotriazin-2-yl)aminofluorescein (DTAF), 2',7'-dimethoxy-4'5'-dichloro-6-carboxyfluorescein (JOE), fluorescein, fluorescein isothiocyanate (FITC), hexachloro-6-carboxyfluorescein (HEX), QFITC (XRITC), tetrachlorofluorescein (TET)), fluoreseamine, IR144, IR1446, Malachite Green isothiocyanate, 4-methylumbelliferone, ortho cresolphthalein, nitrotyrosine, pararosaniline, Phenol Red, B-phycoerythrin, R-phycoerythrin, o-phthaldialdehyde, Oregon Green®, propidium iodide, pyrene and derivatives (pyrene, pyrene butyrate, succinimidyl 1-pyrene butyrate), QSY® 7, QSY® 9, QSY® 21, QSY® 35 (Molecular Probes), Reactive Red 4 (Cibacron® Brilliant Red 3B-A), rhodamine and derivatives (6-carboxy-X-rhodamine (ROX), 6-carboxyrhodamine (R6G), lissamine rhodamine B sulfonyl chloride, rhodamine (Rhod), rhodamine B, rhodamine 123, rhodamine green, rhodamine X isothiocyanate, sulforhodamine B, sulforhodamine 101, sulfonyl chloride derivative of sulforhodamine 101 (Texas Red)), N,N,N',N'-tetramethyl-6-carboxyrhodamine (TAMRA), tetramethyl rhodamine, tetramethyl rhodamine isothiocyanate (TRITC), CAL Fluor Red 610, Quasar 670, riboflavin, rosolic acid, terbium chelate derivatives.

Other fluorescent nucleotide analogs can be used, see, e.g., Jameson, 278 *Meth. Enzymol.*, 363-390 (1997); Zhu, 22 *Nucl. Acids Res.*, 3418-3422 (1994). U.S. Pat. Nos. 5,652,099 and 6,268,132 also describe nucleoside analogs for incorporation into nucleic acids, e.g., DNA and/or RNA, or oligonucleotides, via either enzymatic or chemical synthesis to produce fluorescent oligonucleotides. U.S. Pat. No. 5,135,717 describes phthalocyanine and tetrabenztriazaporphyrin reagents for use as fluorescent labels.

The detectable label can be incorporated into, associated with or conjugated to a nucleic acid. Label can be attached by spacer arms of various lengths to reduce potential steric hindrance or impact on other useful or desired properties. See, e.g., Mansfield, *Mol. Cell. Probes*. 9:145-156 (1995). Detectable labels can be incorporated into nucleic acids by covalent or non-covalent means, e.g., by transcription, such as by random-primer labeling using Klenow polymerase, or nick translation, or amplification, or equivalent as is known in the art. For example, a nucleotide base is conjugated to a detectable moiety, such as a fluorescent dye, and then incorporated into nucleic acids during nucleic acid synthesis or amplification.

With Scorpion™ probes, sequence-specific priming and PCR product detection is achieved using a single molecule.

The Scorpion™ probe maintains a stem-loop configuration in the unhybridized state. The fluorophore is attached to the 5' end and is quenched by a moiety coupled to the 3' end. The 3' portion of the stem also contains sequence that is complementary to the extension product of the primer. This sequence is linked to the 5' end of a specific primer via a non-amplifiable monomer. After extension of the Scorpion™ primer, the specific probe sequence is able to bind to its complement within the extended amplicon thus opening up the hairpin loop. This prevents the fluorescence from being quenched and a signal is observed. A specific target is amplified by the reverse primer and the primer portion of the Scorpion™, resulting in an extension product. A fluorescent signal is generated due to the separation of the fluorophore from the quencher resulting from the binding of the probe element of the Scorpion™ to the extension product.

TaqMan® probes (Heid et al., *Genome Res*, 6:986-994, 1996) use the fluorogenic 5' exonuclease activity of Taq polymerase to measure the amount of target sequences in cDNA samples. TaqMan® probes are oligonucleotides that contain a donor fluorophore usually at or near the 5' base, and a quenching moiety typically at or near the 3' base. The quencher moiety may be a dye such as TAMRA or may be a non-fluorescent molecule such as 4-(4-dimethylaminophenylazo) benzoic acid (DABCYL). See Tyagi et al., *Nature Biotechnology*, 16:49-53 (1998). When irradiated, the excited fluorescent donor transfers energy to the nearby quenching moiety by FRET rather than fluorescing. Thus, the close proximity of the donor and quencher prevents emission of donor fluorescence while the probe is intact.

TaqMan® probes are designed to anneal to an internal region of a PCR product. When the polymerase (e.g., reverse transcriptase) replicates a template on which a TaqMan® probe is bound, its 5' exonuclease activity cleaves the probe. This ends the activity of the quencher (no FRET) and the donor fluorophore starts to emit fluorescence which increases in each cycle proportional to the rate of probe cleavage. Accumulation of PCR product is detected by monitoring the increase in fluorescence of the reporter dye (note that primers are not labeled). If the quencher is an acceptor fluorophore, then accumulation of PCR product can be detected by monitoring the decrease in fluorescence of the acceptor fluorophore.

In a suitable embodiment, real-time PCR is performed using any suitable instrument capable of detecting fluorescence from one or more fluorescent labels. For example, real time detection on the instrument (e.g., a ABI Prism® 7900HT sequence detector) monitors fluorescence and calculates the measure of reporter signal, or Rn value, during each PCR cycle. The threshold cycle, or Ct value, is the cycle at which fluorescence intersects the threshold value. The threshold value is determined by the sequence detection system software or manually. The Ct value may be correlated to the amount of initial template nucleic acid in the reaction.

In some embodiments, melting curve analysis may be used to detect an amplification product. Melting curve analysis involves determining the melting temperature of nucleic acid amplicon by exposing the amplicon to a temperature gradient and observing a detectable signal from a fluorophore. Melting curve analysis is based on the fact that a nucleic acid sequence melts at a characteristic temperature called the melting temperature ($T_m$), which is defined as the temperature at which half of the DNA duplexes have separated into single strands. The melting temperature of a DNA depends primarily upon its nucleotide composition. Thus, DNA molecules rich in G and C nucleotides have a higher $T_m$ than those having an abundance of A and T nucleotides.

Where a fluorescent dye is used to determine the melting temperature of a nucleic acid in the method, the fluorescent dye may emit a signal that can be distinguished from a signal emitted by any other of the different fluorescent dyes that are used to label the oligonucleotides. In some embodiments, the fluorescent dye for determining the melting temperature of a nucleic acid may be excited by different wavelength energy than any other of the different fluorescent dyes that are used to label the oligonucleotides. In some embodiments, the second fluorescent dye for determining the melting temperature of the detected nucleic acid is an intercalating agent. Suitable intercalating agents may include, but are not limited to SYBR™ Green 1 dye, SYBR™ dyes, Pico Green, SYTO dyes, SYTOX dyes, ethidium bromide, ethidium homodimer-1, ethidium homodimer-2, ethidium derivatives, acridine, acridine orange, acridine derivatives, ethidium-acridine heterodimer, ethidium monoazide, propidium iodide, cyanine monomers, 7-aminoactinomycin D, YOYO-1, TOTO-1, YOYO-3, TOTO-3, POPO-1, BOBO-1, POPO-3, BOBO-3, LOLO-1, JOJO-1, cyanine dimers, YO-PRO-1, TO-PRO-1, YO-PRO-3, TO-PRO-3, TO-PRO-5, PO-PRO-1, BO-PRO-1, PO-PRO-3, BO-PRO-3, LO-PRO-1, JO-PRO-1, and mixture thereof. In suitable embodiments, the selected intercalating agent is SYBR™ GREEN 1 dye.

By detecting the temperature at which the fluorescence signal is lost, the melting temperature can be determined. In the disclosed methods, each of the amplified target nucleic acids may have different melting temperatures. For example, each of these amplified target nucleic acids may have a melting temperature that differs by at least about 1° C., more preferably by at least about 2° C., or even more preferably by at least about 4° C. from the melting temperature of any of the other amplified target nucleic acids.

Methods of Diagnosis

In one aspect, the methods described herein provide for diagnosing prostate cancer or a susceptibility to cancer in a subject. The term "diagnose" or "diagnosis" as used herein refers to the act or process of identifying or determining a disease or condition in an organism or the cause of a disease or condition by the evaluation of the signs and symptoms of the disease or disorder. Usually, a diagnosis of a disease or disorder is based on the evaluation of one or more factors and/or symptoms that are indicative of the disease. That is, a diagnosis can be made based on the presence, absence or amount of a factor which is indicative of presence or absence of the disease or condition. Each factor or symptom that is considered to be indicative for the diagnosis of a particular disease does not need be exclusively related to the particular disease, i.e., there may be differential diagnoses that can be inferred from a diagnostic factor or symptom. Likewise, there may be instances where a factor or symptom that is indicative of a particular disease is present in an individual that does not have the particular disease. The methods include, but are not limited to, prostate and lung cancer and translocations, insertions, inversions and deletions associated with those cancers.

In one embodiment, the expression level of the 5' region of the TMPRSS2 gene is compared to the expression level of the 3' region of the TMPRSS2 gene in a sample firm a subject, wherein a difference in the expression levels of the 5' region of the TMPRSS2 gene and the 3' region of the TMPRSS2 gene is indicative of prostate cancer or a susceptibility to prostate cancer in the subject.

Methods of Prognosis

In one aspect, the methods described herein provide a prognosis for cancer or in a subject. The term "prognosis" as used herein refers to a prediction of the probable course and outcome of a clinical condition or disease. A prognosis of a patient is usually made by evaluating factors or symptoms of a disease that are indicative of a favorable or unfavorable course or outcome of the disease. The term prognosis does not refer to the ability to predict the course or outcome of a condition with 100% accuracy. Instead, the skilled artisan will understand that the term "prognosis" refers to an increased probability that a certain course or outcome will occur; that is, that a course or outcome is more likely to occur in a patient exhibiting a given condition, when compared to those individuals not exhibiting the condition. A prognosis may be expressed as the amount of time a patient can be expected to survive. Alternatively, a prognosis may refer to the likelihood that the disease goes into remission or to the amount offline the disease can be expected to remain in remission. Prognosis can be expressed in various ways; for example prognosis can be expressed as a percent chance that a patient wall survive after one year, five years, ten years or the like. Alternatively prognosis may be expressed as the number of years, on average that a patient can expect to survive as a result of a condition or disease. The prognosis of a patient may be considered as an expression of relativism, with many factors affecting the ultimate outcome. For example, for patients with certain conditions, prognosis can be appropriately expressed as the likelihood that a condition may be treatable or curable, or the likelihood that a disease will go into remission, whereas for patients with more severe conditions prognosis may be more appropriately expressed as likelihood of survival for a specified period of time. The methods include, but are not limited to, prostate and lung cancer.

A prognosis is often determined by examining one or more prognostic factors or indicators. These are markers, such as the presence of a particular chromosomal translocation, the presence or amount of which in a patient (or a sample obtained from the patient) signal a probability that a given course or outcome will occur. The skilled artisan will understand that associating a prognostic indicator with a predisposition to an adverse outcome may involve statistical analysis.

In one embodiment, the expression level of the 5' region of the TMPRSS2 gene is compared to the expression level of the 3' region of the TMPRSS2 gene in a sample from a subject, wherein a difference in the expression levels of the 5' region of the TMPRSS2 gene and the 3' region of the TMPRSS2 gene is indicative of stage, severity or outcome of prostate cancer in the subject. Nam et al., Br J. Cancer, 97:16390-1695, 2007, examined prostate cancer specimens from 165 patients who underwent surgery for clinically localized prostate cancer between 1998 and 2006. They tested for the presence of TMPRSS2:ERG gene fusion product and conducted a survival analysis to determine the prognostic significance of the presence of the TMPRSS2:ERG fusion gene on the risk of prostate cancer recurrence, adjusting for the established prognostic factors. The subgroup of patients with the fusion protein had a significantly higher risk of recurrence (58.4% at 5 years) than did patients who lacked the fusion protein (8.1%, P<0.0001). Among prostate cancer patients treated with surgery, the expression of TMPRSS2:ERG fusion gene is a strong prognostic factor and is independent of grade, stage and PSA level. As such, the present methods are useful in providing a prognosis for recurrence of prostate cancer.

Example 1

The examples below illustrate a standard protocol for performing RT-PCR and analyzing in real time. The TaqMan system of probe labeling is an exemplary method of real time detection of PCR amplicons. The following examples serve to illustrate the present invention and is in no way intended to limit the scope of the invention.

Figure 1:
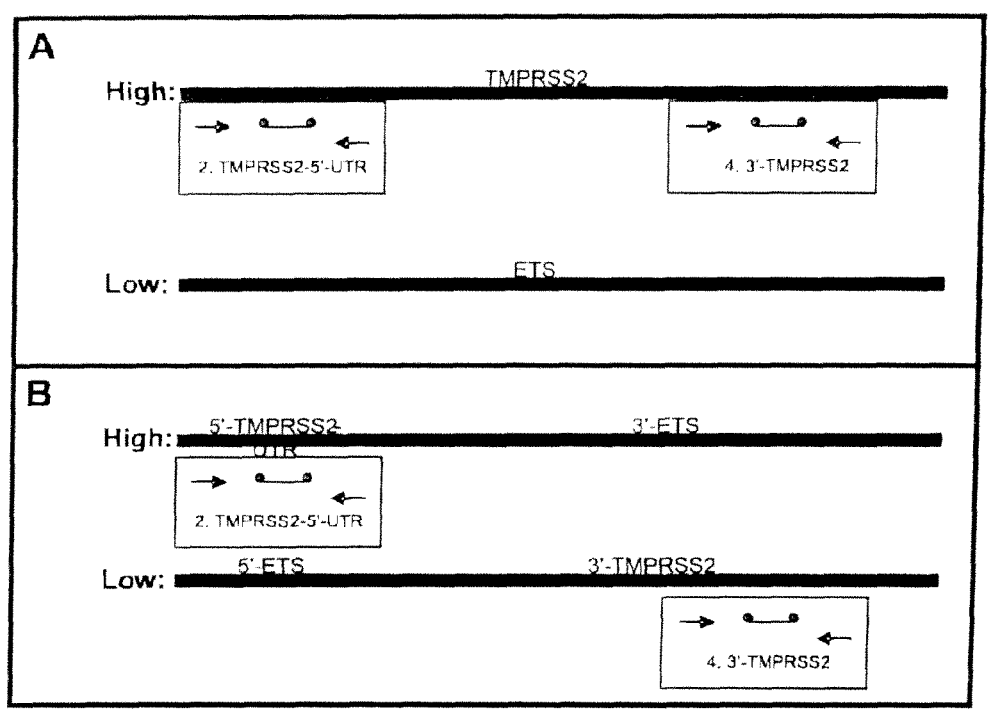
FIG. 1 is a schematic diagram showing the quantitative RT-PCR design for detection of TMPRSS2 translocations.

To detect the presence of translocations or fusions involving TMPRSS2, commonly found fused with ETS transcripts in genetic samples from prostate cancer patients, an approach was taken that identifies breakage of the 5' and 3' portions of TMPRSS2 and the subsequent translocation of the 3' portion to a region under the control of regulatory elements that are less robust than the regulatory elements normally associated with TMPRSS2, ETS (E-Twenty Six) is a family of transcription factors which include, for example, ERG and ETS Translocation Variants (ETV), which include, for example, ETV1, ETV4 and ETV5). TMPRSS2:ERG and TMPRSS2:ETV translocations generally result in expression of a fusion transcript containing at minimum the 5' untranslated region of TMPRSS2 fused to coding regions of ERG and ETV. With this in mind, a real-time RT-PCR assay was designed to separately analyze expression levels of the 5' and 3' regions of TMPRSS2 (FIG. 1). Samples that do not contain a translocation involving TMPRSS2 demonstrate the same expression pattern between the 5' and 3' region because they are linked and under the control of the same regulatory elements (e.g., those contained in the 5' untranslated region) (FIG. 1, Panel A). Samples containing a TMPRSS2 translocation, however, show independent expression patterns for the 5' and 3' region, regardless of the translocation partner, because the two regions are now unlinked and under the control of different regulatory elements (FIG. 1, Panel B). In the case of ERG and ETV translocations, a portion of 3' TMPRSS2, which is normally expressed at high levels in the prostate, has a much lower expression level than in non-translocated samples because it has been fused with the ERG or ETV coding region and regulatory sequences, which normally confers lower level of ERG or ETV expression in the prostate relative to the TMPRSS2 expression. One advantage of this detection system is that the translocation partner for TMPRSS2 need not be identified a priori and separately assessed.

Distinct 3'-TMPRSS2 expression levels expected to be found in samples containing TMPRSS2 translocations and those without translocations can be established by normalizing the expression levels of 3' TMPRSS2 to 5' TMPRSS2. In this study, a TMPRSS2 an IDE Score was calculated according to the following formula:

$$\text{IDE Score} = 2^{-(C_{t\,3'\text{-}TMPRSS2}) - (C_{t\,TMPRSS2\text{-}5'UTR})}$$

wherein the Ct values were obtained by RT-PCR

FIG. 2 shows a dot plot of 25 formalin-fixed and paraffin-embedded (FFPE) tissue samples grouped by TMPRSS2:ERG fusion status. For example, using an IDE cutoff of 80, at least 84% of the tumor specimens (21/25) were accurately identified as fusion negative or positive by the assays of the present invention. Because such a large percentage of individuals with prostate cancer harbor TMPRSS2:ETS fusions, the described assay would be a beneficial tool to diagnose the large majority of prostate cancer cases regardless of the TMPRSS2 fusion type involved.

Example 2

RNA Extraction

RNA from formalin-fixed and paraffin-embedded (FFPE) tissue was extracted by column purification (HighPure miRNA isolation kit, Roche) followed by DNase I digestion (Invitrogen). Plasma RNA was extracted as follows: Study 1: 1 mL plasma from each donor was extracted by NucliSENS® easyMAG® (Biomerieux) followed by DNase I digestion (Invitrogen). Plasma extraction was further optimized in Study 2 as follows: 2 mL plasma from each donor was extracted by NucliSENS® easyMAG® (Biomerieux) followed by DNase I digestion in conjunction with RNA concentration utilizing RNeasy mini kit (Qiagen).

Real-Time RT-PCR

TaqMan primer and probe sets were designed to independently amplify 5' and 3' regions of each gene (TMPRSS2 model shown in FIG. 1). In separate reactions, 5' and 3' transcript regions and an endogenous control were amplified by real-time RT-PCR (RNA Ultrasense, Invitrogen; ABI 7900 Sequence Detector, Applied Biosystems).

Intragenic Differential Expression (IDE) Profile Calculations

Study 1

TMPRSS2 was initially analyzed in FFPE tissue from 20 patients (9 prostate cancer ("PCa") and 11 benign prostate hyperplasia ("BPH")) and plasma from 42 patients (32 PCa and 10 BPH). IDE was expressed as a ratio of 3':5' transcript levels which were determined by real-time RT-PCR. A normal 3':5' ratio (≥30) was established by comparing non-malignant cells to tumor cells from FFPE tissue. This cutoff was subsequently used to identify abnormal ratios in plasma specimens.

Study 2

Detection methods, quantification methods, and IDE calculations were further optimized in the second study. Eight-point standard curves ranging from 1 to 150 ng of PC-3 RNA (Ambion) were used to extrapolate transcript quantities from Ct values. The absolute values of the differences in 5' and 3' levels from the same transcript were calculated using the transcript region quantities as determined by standard curve and normalized to endogenous control (ABL) (Calculation: IDE=(5'/ABL-3'/ABL)-b; where b represents gene-specific normalization value). Normal ranges were determined by analyzing results from normal prostate RNA and known TMPRSS2:ERG fusion positive specimens TMPRSS2 IDE In FFPE Tissue The initial study of 20 FFPE tissue specimens and 42 plasma specimens from patients with prostate cancer or BPH utilized a simple 3':5' ratio cutoff to determined TMPRSS2 Intragenic Differential expression vs. mutual expression of the 2 regions analyzed (Table 1). With a 3':5' ratio cutoff of <30, in FFPE tissue, TMPRSS2 IDE was observed in 100% (9/9) prostate cancer specimens and 9% (1/11) BPH specimens. In plasma, early studies yielded 20 samples with RNA passing QC standards. Of these 20 samples, TMPRSS2 IDE was observed in 47% (7/15) PCa, 60% (9/15) PCa samples were positive for 5', 3', or both regions of TMPRSS2, and 20% (1/5) BPH specimens were positive for 1 region of TMPRSS2.

TABLE 1

Initial IDE determinations of TMPRSS2 in BPH and PCa specimens

| Specimen | 3' or 5' Detected | 3':5' ≥30 | 3':5' <30 | 3':5' = UD |
|---|---|---|---|---|
| FFPE Tissue | | | | |
| BPH | 100% (11/11) | 91% (10/11) | 9% (1/11) | 0% (0/11) |
| PCa | 100% (9/9) | 0% (0/9) | 100% (9/9) | 0% (0/9) |
| Plasma | | | | |
| BPH | 20% (1/5) | NA | NA | 100% (5/5) |
| PCa | 60% (9/15) | 6.7 (1/15) | 47% (7/15) | 47% (7/15) |

UD, undetected (3' only or no 5' or 3').

Optimization of the entire assay provided a better means for quantification of IDE and the initial studies were repeated and expanded. With the improved assay TMPRSS2 IDE was first evaluated in normal prostate and a confirmed TMPRSS2:ERG positive prostate cancer cell line (VCaP, ATCC) (FIG. 3). As expected, normal prostate TMPRSS2 and ERG showed no very low IDE scores whereas VCaP cells showed the expected pattern of high positive TMPRSS2 score (meaning 5'>3') and a highly negative ERG score (meaning 3'>5'). For ease of analysis, further IDE scores are expressed as absolute values.

RNA was purified from 52 FFPE tissue samples (32 PCa. 14 BPH, 6 initially diagnosed as BPH but upon further review were determined to be atypical or have PIN) and analyzed for TMPRSS2:ERG fusion by direct fusion detection (TMPRSS2 exon 1:ERG exon 4) and by TMPRSS2 IDE. TMPRSS2 IDE scores were significantly higher in PCa (mean=1.6, SE=0.5) vs. BPH (mean=0.28, SE=0.06) (FIG. 4). Likewise, ERG IDE scores were also significantly higher in PCa vs. BPH (FIG. 5). Direct TMPRSS2:ERG fusion detection revealed 56% (18/32) positive PCa specimens and no positive BPH (14) or atypical/PIN (6) specimens (Table 2). With a cutoff of 0.25 (IDE>0.25), TMPRSS2 IDE was observed in 84% PCa (26/31), 67% Atypical/PIN (4/6) and 36% BPH (5/14) (Table 2).

TABLE 2

Detection of TMPRSS2 rearrangements by in FFPE tissue

|  | TMPRSS2:ERG | | TMPRSS2 IDE | |
|---|---|---|---|---|
| Diagnosis | − | + | <0.25 | >0.25 |
| BPH | 100% (14/14) | 0% (0/14) | 71% (10/14) | 36% (5/14) |
| Prostate Cancer | 44% (14/32) | 56% (18/32) | 23% (7/31) | 84% (26/31) |
| Atypical/PIN | 100% (6/6) | 0% (0/6) | 33% (2/6) | 67% (4/6) |

TMPRSS2 Detection in Plasma

Plasma specimens were also assayed for the presence of TMPRSS2:ERG, and 5' UTR and 3' coding regions of TMPRSS2. RNA was extracted from 1 ml (Study 1) or 2 mL (Study 2) plasma from a total of 67 specimens (42 PCa and 17 BPH). Results from samples that sufficiently amplified endogenous control are shown in Table 3. Clearly, Study 2 resulted in a higher rate of detection of 5' UTR or 3' coding region of TMPRSS2 with 78% (7/9) positive PCa and 0% (0/3) BPH as compared to 44% PCa and 17% BPH in Study 1. Most notably however, analyzing expression of both 5' UTR and 3' coding regions of TMPRSS2 increases the number of positive specimens by approximately 10-15% compared to detection of 5' UTR or 3' coding region alone and demonstrates significant improvement over detection of TMPRSS2:ERG fusion where only 1 positive PCa specimen was found. Overall, TMPRSS2 was detected in plasma from 44-78% of PCa and 0-17% of BPH specimens.

TABLE 3

Detection of TMPRSS2:ERG fusion and 5' and 3' TMPRSS2 in plasma

| TMPRSS2 Region Detected | BPH | PCa |
|---|---|---|
| Study 1 | 6 | 27 |
| TMPRSS2:ERG fusion | 0% (0/6) | 4% (1/27) |
| 5' UTR | 0% (0/6) | 37% (10/27) |
| 3' coding | 17% (1/6) | 30% (8/27) |
| 5' UTR and 3' coding | 0% (0/6) | 19% (6/27) |
| 5' UTR or 3' coding | 17% (1/6) | 44% (12/27) |
| Study 2 | 3 | 9 |
| TMPRSS2:ERG fusion | 0% (0/3) | 0% (0/9) |
| 5' UTR | 0% (0/3) | 67% (6/9) |
| 3' coding | 0% (0/3) | 67% (6/9) |
| 5' UTR and 3' coding | 0% (0/3) | 56% (5/9) |
| 5' UTR or 3' coding | 0% (0/3) | 78% (7/9) |

ERG and ETV1 IDE in FFPE Tissue

The TMPRSS2 IDE strategy was extended to ETS transcription factors. In particular, ERG demonstrated significant differences in PCa specimens (mean=14.6 SE=5.5) as compared to BPH (mean=0.27, SE=0.03) (FIG. 5). With a cutoff of 0.4 (IDE>0.4), ERG IDE was observed in 97% PCa (29/30), 0% Atypical/PIN (0/5) and 7% BPH (1/14) (Table 4). ETV1 IDE (IDE score>0.08) was less frequent in PCa, where it was found in 30% (9/30) of specimens, but was also observed 14% BPH (2/14) and 20% Atypical/PIN (1/5). All prostate cancer specimens were positive for at least one of the markers tested, 80% were positive for at least two of the markers, and 24% were positive for all three (Table 5). No BPH specimens were positive for more than one marker.

TABLE 4

Detection of ERG and ETV1 IDE in FFPE Tissue

|  | ERG IDE | | ETV1 IDE | |
|---|---|---|---|---|
| Diagnosis | <0.40 | >0.40 | ≤0.08 | >0.08 |
| BPH | 93% (13/14) | 7% (1/14) | 86% (12/14) | 14% (2/14) |
| Prostate Cancer | 3% (1/30) | 97% (29/10) | 70% (23/30) | 30% (9/30) |
| Atypical/PIN | 100% (5/5) | 0% (0/5) | 80% (4/5) | 20% (1/5) |

TABLE 5

Frequency of Single or Multiple IDE Scores in FFPE Tissue

|  | IDE Panel | | | |
|---|---|---|---|---|
| Diagnosis | Negative | ≥1 Positive | ≥2 Positive | 3 Positive |
| BPH | 50% (7/14) | 50% (7/14) | 7% (1/14) | 0% (0/14) |
| Prostate Cancer | 0% (0/30) | 100% (30/30) | 80% (24/30) | 27% (8/30) |
| Atypical/PIN | 20% (1/5) | 67% (4/6) | 20% (1/5) | 0% (0/5) |

TABLE 6

Amplification Primers and Probes for IDE Analysis

| 5' TMPRSS2 UTR | |
|---|---|
| 5' TMPRSS2 Forward | TAGGCGCGAGCTAAGCAGGA (SEQ ID NO: 1) |
| 5' TMPRSS2 Reverse | CCTGCCGCGCTCCAGGCGG (SEQ ID NO: 2) |
| 5' TMPRSS2 Probe | AGGCGGAGGCGGAGGGCGAGGGGC (SEQ ID NO: 3) |
| 3' TMPRSS2 | |
| 3' TMPRSS2 Forward | TGGTGCGAGGGAAGCAAT (SEQ ID NO: 4) |
| 3' TMPRSS2 Reverse | CACCCAATGTGCAGGTGGA (SEQ ID NO: 5) |
| 3' TMPRSS2 Probe | AAAGGAACTTGCCCTGAGCACTCC (SEQ ID NO: 6) |
| 5' ERG | |
| 5' ERG Forward | CATCCGCTCTAAACAACCTCA (SEQ ID NO: 7) |
| 5' ERG Reverse | GGCCATAATGCGATCAAGTT (SEQ ID NO: 8) |
| 5' ERG Probe | CTTTCTGGTCAGAGAGAAGCAA (SEQ ID NO: 9) |
| 3' ERG | |
| 3' ERG Forward | CCAGGTGAATCGCTCAAGGAA (SEQ ID NO: 10) |
| 3' ERG Reverse | GGGCTGCCCACCATCTTC (SEQ ID NO: 11) |
| 3' ERG Probe | TCTCCTGATGAATGCAGTGTGGCC (SEQ ID NO: 12) |

Conclusions

Intragenic differential expression (IDE) of TMPRSS2 as well as ERG are significantly higher in prostate cancer specimens as compared to normal prostate and BPH. By establishing a cutoff for normal vs. abnormal IDE scores, we were able to detect TMPRSS2 differences in FFPE tissue from 77% of prostate cancer samples while present in 29% of BPH samples. Even higher sensitivity and specificity was achieved with ERG where elevated IDE scores were detected in 97% of prostate cancer samples and only 1 (7%) BPH specimen. The high percentage of PCa specimens with elevated ERG IDE scores may be attributed to translocations with TMPRSS2 as well as other yet to be identified 5' fusion partners such as those recently found to be involved in ETV1 and ETV5 gene fusions, including the 5' UTRs from SLC45A3, HERV-K_22q11.3, C15ORF21, and HNRPA2B1 (Helgeson et al. 2008 and Tomlins 2007).

IDEs in TMPRSS2 and ETV1 showed unexpected patterns in some samples. Invariably, ERG IDE was in the orientation of the 3' transcript region being present at higher levels than 5' levels, as would be expected from the understanding that the consequence of TMPRSS2 translocation (and other 5' translocation partners) is an increase in levels of the partnered ETS transcription factor. Alternatively, TMPRSS2 and ETV1 seemed to demonstrate more complexity in that not only were the expected IDE orientations observed, but the reverse orientations were also observed in many samples, meaning that the 5' region of ETV1 and the 3' region of TMPRSS2 were at higher levels than their respective counterpart. This difference may underlie the observation that TMPRSS2:ETV1 translocations are rarely found when assaying directly for the fusion. Due to these variations, the IDE values are expressed as an absolute value to account for differences in both orientations. Notably, all BPH and Atypical/PIN specimens that were positive for ETV1 IDE demonstrated the reverse orientation while both orientations were observed in prostate cancer samples. Additionally, over one quarter of the prostate cancer samples demonstrated IDE in both ETV1 and ERG. This may be due to the presence of multiple focal points or multiple clonalities in a single specimen. It is apparent however, that ERG IDE is observed primarily in confirmed prostate cancer and was only observed in one BPH specimen.

These plasma sample studies (Study 1 and Study 2 described above) demonstrated that 5' or 3' TMPRSS2 could be detected in 44% (Study 1) and 78% (Study 2) of specimens from prostate cancer patients, when both regions were assessed, as compared to 30-37% (Study 1) and 67% (Study 2) when assaying for only one region of TMPRSS2. By assaying for both regions of TMPRSS2 and by improving extraction and detection methods, we were able to increase the number of plasma specimens in which TMPRSS2 was detected. TMPRSS2 was detected in only one BPH specimen from Study 1 and no BPH specimens in Study 2. The 5' UTR and 3' coding region of TMPRSS2 in normal and BPH urine specimens have been successfully amplified for evaluation using this IDE methodology.

Example 3

A fusion gene with transforming activity, echinoderm microtubule associated protein like 4-anaplastic lymphoma kinase (EML4-ALK), is found in approximately 5% of NSCLCs of lung cancer patients. The presence of the EML4-ALK fusion can be predictive of the response of these patients to certain therapies. We applied the IDE methodology to test the ability of using IDE to identify patients with potential ALK translocation, not limited to know variants or fusion partners. Patient lung cancer tissue samples were analyzed using the IDE methodology by determining the ALK IDE cutoff value and then comparing the calculated cutoff to the ALK IDE values from lung cancer tissue samples. The positive results were further analyzed by direct detection of EML4-ALK fusions using RT-PCR. Finally, a subset of the NSCLC positive samples were screened by immunohistochemistry (IHC) and/or fluorescence in situ hybridization (FISH).

ALK IDE Cutoff Determination

ALK IDE was analyzed in lung cancer tissue samples from 56 NSCLC patients. ALK IDE scores are expressed as a ratio of 3'5' transcript levels determined by real-time RT-PCR. The ALK IDE scores were calculated by, first, determining 5' and 3' ALK transcript levels using RT-PCR and, second, normalizing those ALK transcript levels using the transcript levels of an endogenous control (ABL) (IDE=5'-ALK/ABL-3'-ALK/ABL). Using an EML4:ALK fusion-positive cell line (NCI-H2228), a positive control ALK IDE 3':5' ratio score of 0.7 was established. This ALK IDE cutoff value of 7 was subsequently used to identify abnormal ratios in tissue specimens, indicating the presence of ALK rearrangement. Further verification of the methodology confirmed that the ALK IDE value was 0.0 in two EML4-ALK negative NSCLC cell lines (NCI-H838 and NCI-H1299).

TABLE 7

ALK Amplification Primers and Probes for IDE Analysis

| 3' ALK Primers | |
| --- | --- |
| 3' ALK Forward | CCCAACTTTGCCATCATTTT (SEQ ID NO: 13) |
| 3' ALK Reverse | GCAAAGCGGTGTTGATTACA (SEQ ID NO: 14) |
| 3' ALK Probe | FAM-TGAATACTGCACCCAGGACC-BHQ (SEQ ID NO: 15) |
| 5' ALK Primers | |
| 5' ALK Forward | TGGCTTTTGACAATATCTCCA (SEQ ID NO: 16) |
| 5' ALK Reverse | TGCAGGATCTTGTCCTCTCC (SEQ ID NO: 17) |
| 5' ALK Probe | AGCCTGGACTGCTACCTCAC (SEQ ID NO: 18) |

ALK IDE In Lung Cancer Tissue

Using the ALK IDE 3':5' ratio cutoff of >0.7, in EML4-ALK fusion-positive cell lines, a diagnostically positive ALK IDE was observed in 11% (6/56) of lung cancer tissue specimens. We tested these six positive samples for direct detection of EML4-ALK fusions by fragment analysis using in-house designed RT-PCR primer sets (FIG. 6). Of the six, EML4-ALK fusions were observed in 83% (5/6) of the samples.

Immunohistochemistry (IHC) and/or Fluorescence In Situ Hybridization (FISH)

A subset of the NSCLC positive samples were screened by IHC and/or FISH (subset results are shown in FIG. 7). The five confirmed ALK IDE positive samples and an additional five samples with slightly to moderate elevated levels of ALK transcript (i.e., ALK IDE>0.1) were further analyzed by FISH. Eight of the ten samples showed ALK rearrangement and/or ALK gene amplification. Three samples interpreted as having ALK rearrangements by FISH were also positive using ALK IDE. Two other ALK IDE positive samples (one confirmed and one unconfirmed by direct RT-PCR) were interpreted as rearrangement negative by FISH.

Conclusions

The application of IDE methodology to ALK is useful for identification of ALK expression and chromosomal rearrangement. ALK IDE accurately categorized all FISH-confirmed rearrangements as positive and detected rearrangements in at least one other confirmed case not identified by FISH. The IDE methodology functions as a universal molecular assay for determining ALK rearrangements in multiple tumor types. This information can be further used by physicians in deciding appropriate therapies for patients.

Other Embodiments

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and genetically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

The inventions illustratively described herein may suitably be practiced in the absence of any element or elements, limitation or limitations, not specifically disclosed herein. Thus, for example, the terms "comprising", "including," containing", etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the invention claimed.

Other embodiments are set forth within the following claims.

What is claimed is:

1. A kit comprising:
    (a) a 5' target primer pair that is complementary to a 5' region of a TMPRSS2 gene transcript, wherein a first primer of the 5' target primer pair comprises the sequence of SEQ ID NO: 1 and a second primer of the 5' target primer pair comprises the sequence of SEQ ID NO: 2;
    (b) an oligonucleotide probe that is complementary to an amplification product generated using the 5' target primer pair, and labeled with a donor fluorophore and a quenching moiety;
    (c) a 3' target primer pair that is complementary to a 3' region of the TMPRSS2 gene transcript, wherein a first primer of the 3' target primer pair comprises the sequence of SEQ ID NO: 5 and a second primer of the 3' target primer pair comprises the sequence of SEQ ID NO: 6; and
    (d) an oligonucleotide probe that is complementary to an amplification product generated using the 3' target primer pair, and labeled with a donor fluorophore and a quenching moiety.

2. The kit of claim 1, further comprising one or more reagents for performing a nucleic acid amplification reaction.

3. The kit of claim 1, wherein the oligonucleotide probe that is complementary to an amplification product of (a) comprises the sequence of SEQ ID NO: 3 and/or the oligonucleotide probe that is complementary to an amplification product of (c) comprises the sequence of SEQ ID NO: 6.

4. A kit comprising:
    (a) a 5' target primer pair that is complementary to a 5' region of a ERG gene transcript wherein a first primer of the 5' target primer pair comprises SEQ ID NO: 7 and a second primer of the 5' target primer pair comprises SEQ ID NO: 8;
    (b) an oligonucleotide probe that is complementary to an amplification product generated using the 5' target primer pair, and labeled with a donor fluorophore and a quenching moiety;
    (c) a 3' target primer pair that is complementary to a 3' region of the ERG gene transcript wherein a first primer of the 3' target primer pair comprises SEQ ID NO: 10 and a second primer of the 3' target primer pair comprises SEQ ID NO: 11; and
    (d) an oligonucleotide probe that is complementary to an amplification product generated using the 3' target primer pair, and labeled with a donor fluorophore and a quenching moiety.

5. The kit of claim 4, wherein the oligonucleotide probe that is complementary to an amplification product of (a) comprises the sequence of SEQ ID NO: 9 and/or the oligonucleotide probe that that is complementary to an amplification product of (c) comprises the sequence of SEQ ID NO: 12.

6. The kit of claim 4, further comprising one or more reagents for performing a nucleic acid amplification reaction.

7. A kit comprising:
    (a) a 5' target primer pair that is complementary to a 5' region of a ALK gene transcript wherein a first primer of the 5' target primer pair comprises the sequence of SEQ ID NO: 13 and a second primer of the 5' target primer pair comprises the sequence of SEQ ID NO: 14;

(b) an oligonucleotide probe that is complementary to an amplification product generated using the 5' target primer pair, and labeled with a donor fluorophore and a quenching moiety;
(c) a 3' target primer pair that is complementary to a 3' region of the ALK gene transcript wherein a first primer of the 3' target primer pair comprises the sequence of SEQ ID NO: 16 and a second primer of the 3' target primer pair comprises the sequence of SEQ ID NO: 17; and
(d) an oligonucleotide probe that is complementary to an amplification product generated using the 3' target primer pair, and labeled with a donor fluorophore and a quenching moiety.

8. The kit of claim 7, wherein the oligonucleotide probe that is complementary to an amplification product of (a) comprises the sequence of the sequence of SEQ ID NO: 15 and/or that is complementary to an amplification product of (c) comprises the sequence of SEQ ID NO: 18.

9. The kit of claim 7, further comprising one or more reagents for performing a nucleic acid amplification reaction.

\* \* \* \* \*